(12) United States Patent
Kovtun et al.

(10) Patent No.: US 6,785,573 B2
(45) Date of Patent: Aug. 31, 2004

(54) LOW DISTORTION ECG FILTER

(75) Inventors: Vladimir V. Kovtun, Eagan, MN (US); Randall Dodson, New Hope, MN (US); Joseph E. Bange, Eagan, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 101 days.

(21) Appl. No.: 10/313,714

(22) Filed: Dec. 9, 2002

(65) Prior Publication Data

US 2003/0083583 A1 May 1, 2003

Related U.S. Application Data

(62) Division of application No. 09/620,663, filed on Jul. 20, 2000, now Pat. No. 6,512,944.

(51) Int. Cl.$^7$ .................................................. A61B 5/04
(52) U.S. Cl. ....................................................... 600/509
(58) Field of Search ................................. 600/323, 508, 600/509, 513, 516, 520; 128/901

(56) References Cited

U.S. PATENT DOCUMENTS

| | | | | |
|---|---|---|---|---|
| 4,630,204 A | * | 12/1986 | Mortara | 600/516 |
| 5,511,553 A | * | 4/1996 | Segalowitz | 600/508 |
| 6,280,391 B1 | * | 8/2001 | Olson et al. | 600/509 |
| 6,339,715 B1 | * | 1/2002 | Bahr et al. | 600/323 |

* cited by examiner

Primary Examiner—George Manuel
(74) Attorney, Agent, or Firm—Thomas J. Nikolai; Nikolai & Mersereau, P.A.

(57) ABSTRACT

A low pass filter especially adapted for use with ECG equipment designed to negate any noise energy that may be superimposed upon the ECG signal itself. A plurality of low-pass FIR filter stages are connected in tandem between a signal input point and a signal output point where each of the stages has a distinct cut-off frequency characteristic. Means are provided for selectively turning ones of the plurality of stages on or off.

2 Claims, 31 Drawing Sheets

NOTES:

— TIME DELAY OF ONE SAMPLE PERIOD

N_FIR — NUMBER OF FIR FILTER TAPS

X(n) — CURRENT SAMPLE

X(n-1) — PREVIOUS SAMPLE, ONE SAMPLE PERIOD OLD

X(n-2) — PREVIOUS SAMPLE, TWO SAMPLE PERIODS OLD

— MULTIPLIER $Ci_0$ — COEFFICIENT (CONSTANT)

— SUMMER (ADDER)

— ABSOLUTE VALUE

— ADDER

LOW DISTORTION ECG FILTER

CROSS-REFERENCE TO RELATED APPLICATION

This application is a divisional of application Ser. No. 09/620,663, filed Jul. 20, 2000, now U.S. Pat. No. 6,512,944 and entitled "LOW DISTORTION ECG FILTER".

BACKGROUND OF THE INVENTION

I. Field of the Invention

This invention relates generally to signal processing apparatus, and more particularly to apparatus for removing noise signal components from noisy analog electrocardiograph (ECG) signals derived from body contacting electrodes without significantly distorting the ECG signal itself

II. Discussion of the Prior Art

Patients having an implanted cardiac rhythm management device, such as a pacemaker or a pacemaker/defibrillator, are periodically monitored using a telemetry link to read out information from the implanted device to an external programmer. Real-time telemetry of measured data is available in most modern pacer systems, including an assessment of battery voltage, current and impedance as well as lead impedance. These are useful measures in diagnosing and anticipating problems with a pacer system. Telemetry of event counters and histograms may be especially useful in evaluating the percentage of time that a patient spends in a particular rhythm or at a particular rate. In this fashion, electrograms having paced events, sensed events and marker channel data can be read out using a telemetry wand positioned over the implanted device.

It is also quite common to affix surface electrodes to the patient to obtain ECG surface data for presentation on a display screen or strip chart recorder for comparison purposes. The analog output signals from the surface electrodes are often contaminated by ambient noise, such as 60 Hz noise from lighting and other AC power sources. Muscle and motion artifacts may also be a source of noise contamination to the ECG signal resulting from cardiac depolarization or repolarization.

It is common practice to utilize filtering techniques in an attempt to isolate the ECG signal itself from whatever noise may be superimposed thereon. However, to date, insufficient attention has been paid to the differences between devices for addressing bradycardia and those for addressing tachycardia. While pacemakers for treating bradycardia deal mostly with conductance problems of the heart, anti-tachy devices deal with the problems in the heart tissue. The surface ECG data for brady devices exhibits a lower heart rate and wider QRS complexes and PR intervals, whereas the ECG data for anti-tachy devices has higher heart rates, shorter QRS complexes and some high frequency oscillations. Thus, a higher quality low-pass filter is required for stripping noise components from ECG signals of anti-tachy devices to address the high frequency components of the ECG signal. It is a principal object of this invention to provide an improved, low-pass filter capable of removing noise signal components from higher frequency ECG signals obtained from tachycardia patients without distorting the ECG signal itself.

SUMMARY OF THE INVENTION

A low-pass filter in accordance with the present invention comprises a plurality of digital filter stages, each with a different cut-off frequency, and connected in tandem between a signal source and a signal output point. Each of the filter stages includes a time delay buffer operative to receive digital data representing sampled values of an analog input signal for at least temporarily storing said sampled values for predetermined time intervals. Responsive to the digital data representing sampled values contained in the time delay buffer is a means for developing an average over time noise signal component that falls within a predetermined frequency band. Each of the plural stages also includes a means for selectively subtracting the average over time noise signal component from a sampled value resident in the time delay buffer to thereby effectively remove the noise component from the stored sampled value.

The average over time noise signal component is preferably derived using a high-pass filter adapted to receive the digital data representing the sampled values stored in the time delay buffer and having a dynamic noise level calculator operative to receive filtered data from the high-pass filter and averaging the filtered data over time.

DESCRIPTION OF THE DRAWINGS

The foregoing features, objects and advantages of the invention will become more apparent to those skilled in the art from the following detailed description of a preferred embodiment, especially when considered in conjunction with the accompanying drawings in which.

DESCRIPTION OF THE PREFERRED EMBODIMENT

While the following description describes the improved low-pass filter of the present invention with the aid of a hardware block diagram, in actual practice, the invention can readily be implemented in software executable by a microprocessor having RAM memory for storing programmable operands and intermediate calculations and a ROM memory for storing a program of instructions executable by the microprocessor or digital signal processor for performing digital signal processing operations. The claims appended hereto are to be interpreted as covering both hardware and software implementations.

Figure 1:
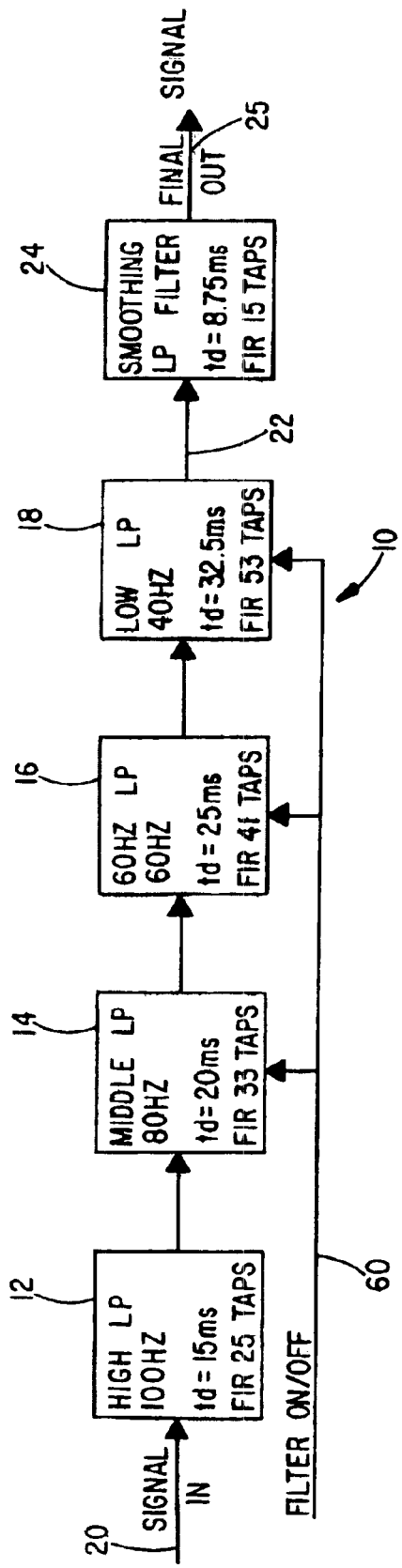
FIG. 1 is a block diagram representation of a low-pass filter for use in a programmer designed for an automatic implantable cardiac defibrillator (AICD) device that is constructed in accordance with the present invention.

Referring first to FIG. 1 there is illustrated by means of a block diagram the high quality low-pass filter 10 comprising the present invention. It is seen to include a plurality of individual low-pass filter stages 12, 14, 16 and 18 connected in tandem between a signal input 20 and a signal output 22. Each of the stages 12, 14, 16 and 18 comprises a low-pass filter having different cut-off frequencies. Specifically, the stage 12 may be a low-pass finite impulse response (FIR) filter designed to have a cut-off frequency of 100 Hz. The next stage, stage 14, may typically be a low-pass FIR filter having a cut-off frequency of 80 Hz. Stage 16 will also be a finite impulse response filter with a cut-off frequency of 60 Hz. Low-pass FIR filter stage 18 then may have a cut-off frequency of 40 Hz. An additional low-pass smoothing filter 24 having a cut-off frequency of about 100 Hz may be connected to the output 22, but that filter is structurally different from the previous four filtering stages.

A finite impulse response filter is a linear discrete time system that forms its output as the weighted sum of the most recent, and a finite number of past, inputs. Time-invariant FIR filters have finite memory, and their impulse response, namely, their response to discrete input that is unity at the first sample and otherwise zero, matches the fixed weighting coefficients of the filter. Time-variant FIR filters, on the other hand, may operate at various sampling rates and/or have weighting coefficients that adapt in accordance with some statistical property of the environment in which they are applied.

Stages 14, 16 and 18 each have control inputs allowing those individual stages to be turned on or off by the application of a binary 1 or 0 signal thereto, respectively. No control input is applied to stage 12 in that it is always wanted that the frequency components greater than 100 Hz be attenuated. It is a unique property of the ECG filter of this invention that it exhibits a constant time delay irrespective of whether the controlled stages are on or off As such, there is not tendency for the ECG signal to shift in position relative to an electrogram trace when the two are being simultaneously displayed on a monitor screen.

The input signal at terminal 20 typically will be sampled outputs from an A/D converter (not shown) where the amplitude of the input waveform from the ECG electrodes is indicated by a digital quantity corresponding to the amplitude of the input waveform at discrete sampling times. Without limitation, the analog input waveform may be sampled every 1.25 ms.

Figure 2:
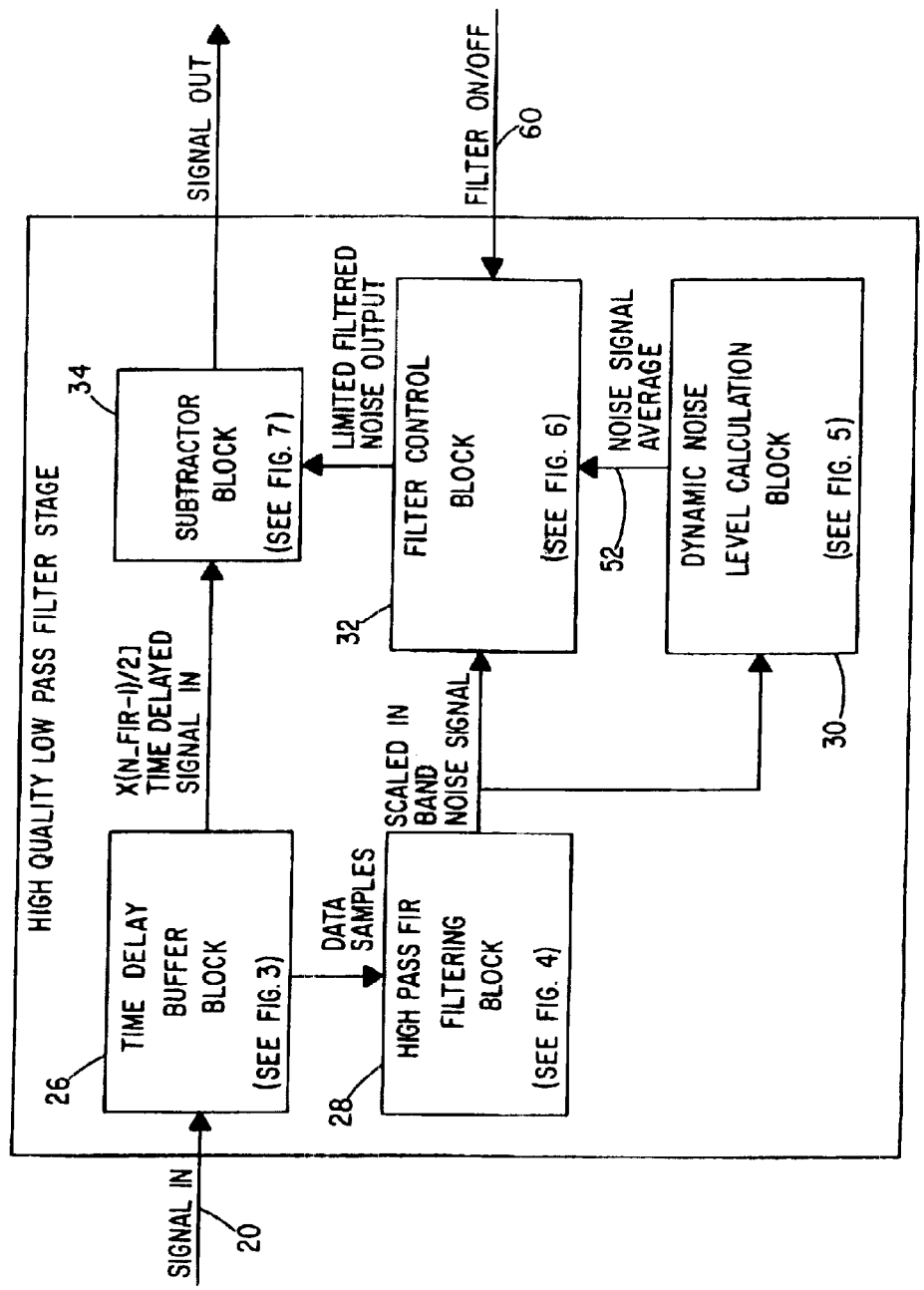
FIG. 2 is a block diagram typical of each of the low-pass filter blocks illustrated in FIG. 1.

Turning next to FIG. 2, there is indicated the make-up of each of the individual stages 12, 14, 16 and 18. Digital data from the analog-to-digital converter is applied via line 20 to a time delay buffer 26 which functions to hold the digital data for a predetermined time interval that is equal to or less than the sampling time of the A/D converter being employed. The digital data temporarily stored in the buffer 26 is subjected to a high-pass filtering operation represented by the high-pass FIR filtering block 28 which functions to calculate a noise level signal for the particular frequency band involved, i.e., 100 Hz for filter stage 12, 80 Hz for filter stage 14, etc. in the exemplary embodiment of FIG. 1. The noise level signal calculated by the high-pass FIR filtering block 28 is scaled and, over time, an average noise level signal is calculated and upper and lower noise bound values are generated by the dynamic noise level calculation block 30.

The scaled in-band noise signal resulting from the high-pass FIR filtering operation (block 28) is applied to a filter control block 32 and in the case of low-pass filter stages 14, 16 and 18 (FIG. 1) an On/Off switch setting control signal is also applied. This control circuit 32 then determines whether the scaled in-band noise signal is to be subtracted from the ECG data then resident in the time delay buffer 26. Thus, the control block 32 operates to prevent subtraction by subtracter 34 of wanted components of the ECG data as it subtracts the noise components.

Referring next to FIGS. 3–7 and the symbol key of FIG. 8, a hardware/software implementation of the time delay buffer 26, the high-pass FIR filtering block 28, the dynamic noise level calculation block 30, the filter control block 32 and the subtracter 34 will be explained.

The time delay buffer 26 receives and stores the digital data indicative of the amplitude of the applied analog signal at a sampling time determined by an analog-to-digital converter (not shown). This data is delayed in time one sample period, T, such that a current sample, x(n), is applied on line 36, the immediately preceding sample x(n−1) appears on line 38, etc. The length of the time delay buffer 26 is equal to the number of taps of the FIR filter 28 used in the particular low-pass filter stage 12, 14, 16, 18. In establishing the number of taps for the several filter stages, consideration is given to the quality of the filtering desired, i.e., how sharp the filtered transitions are between the pass band and stop band regions. Another consideration is the processing capability of the microprocessor involved. As the number of taps increases, so, too, does the number of multiply and add operations during each sample period. The degree of phase linearity is also taken into account in arriving at the number of taps for the various filter stages illustrated in FIG. 1. Thus, for the low-pass filter stage 12, illustrated in FIG. 1 as including 25 taps, would dictate that the time delay buffer stored the current sample through the previous 24 samples. ((X)N_FIR-1) on line 40.

Figure 3:
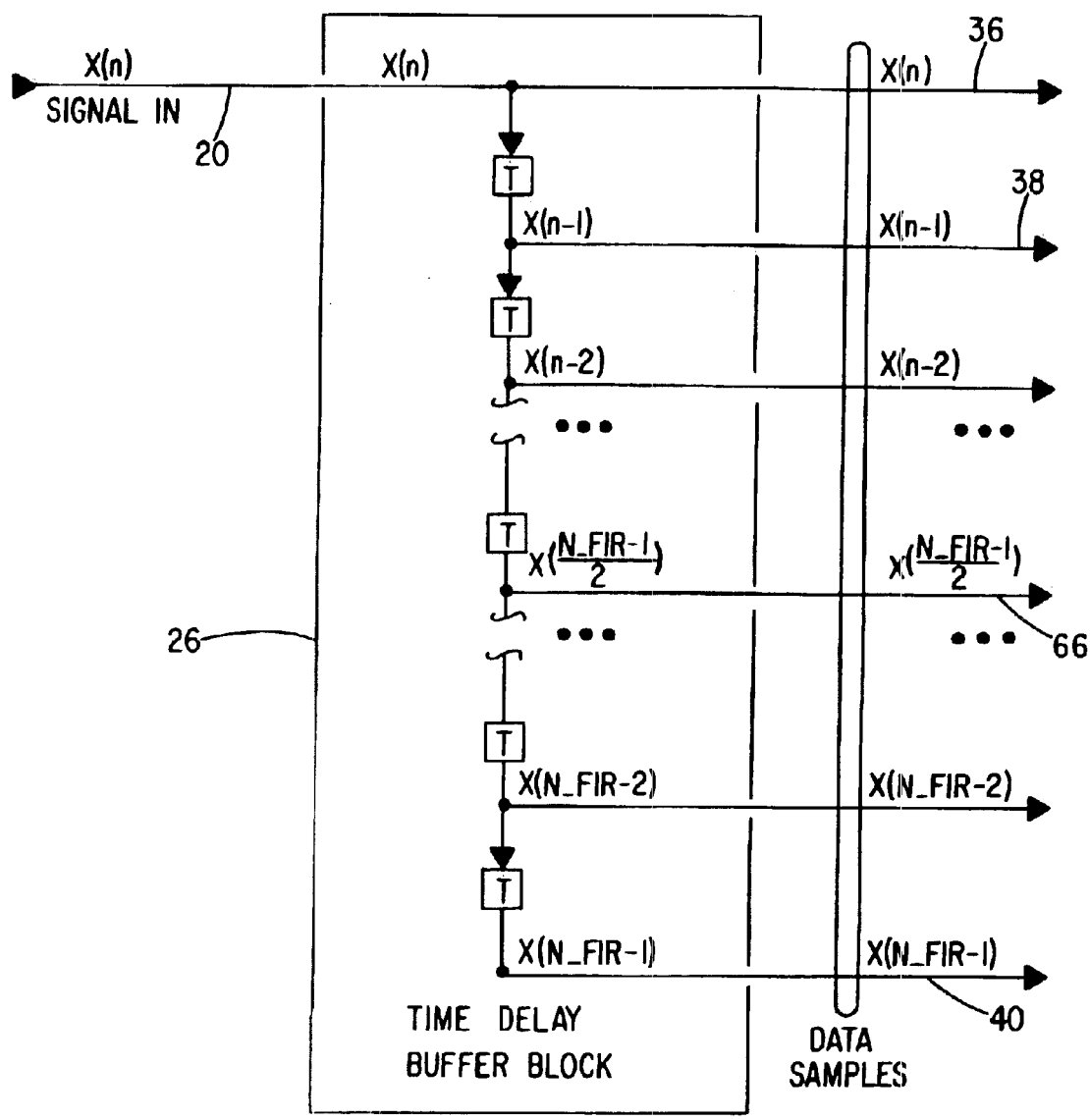
FIG. 3 is a block diagram representation of a time delay buffer incorporated in the low-pass filter stage of FIG. 2.
Figure 4:
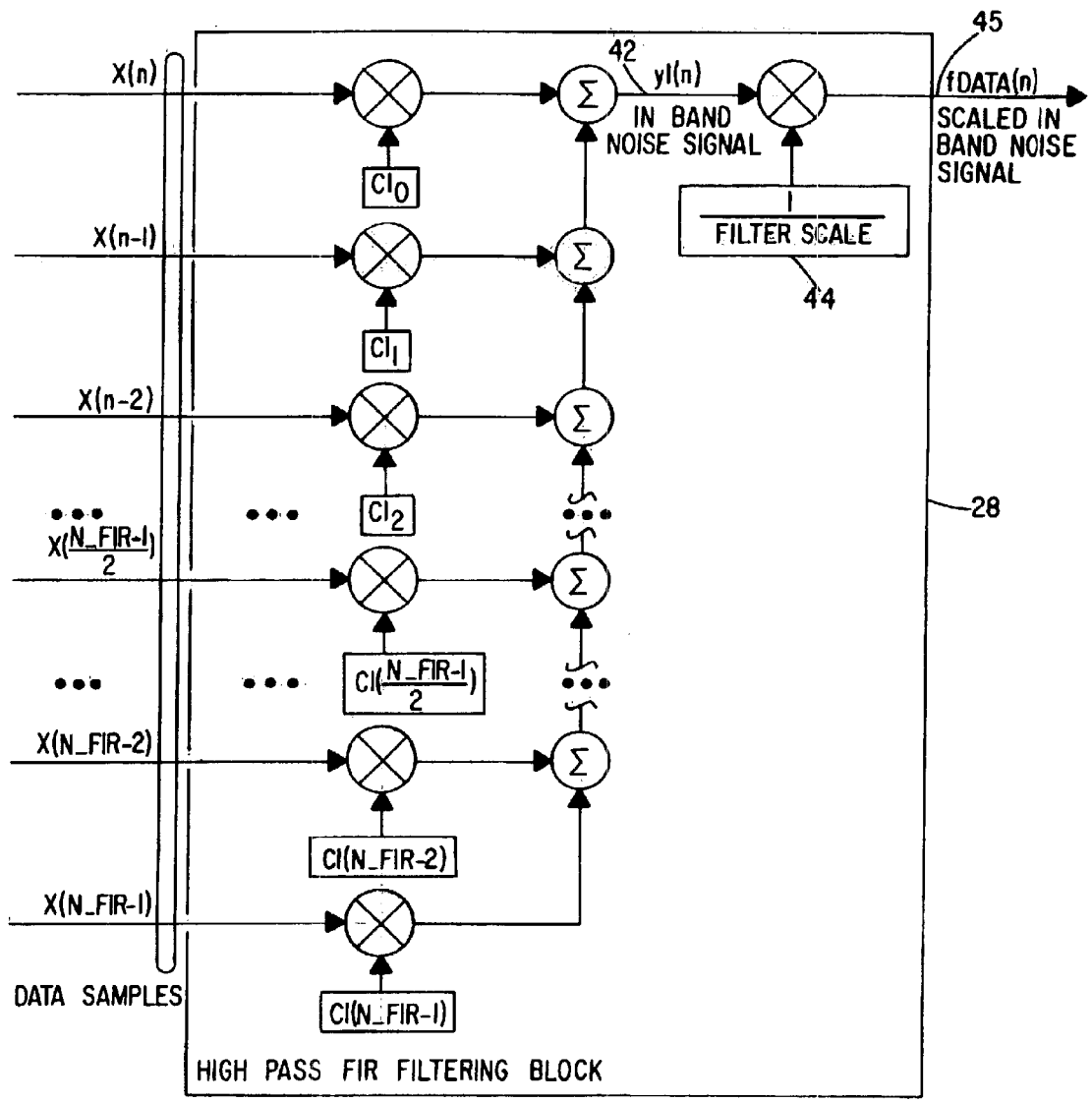
FIG. 4 is a block diagram representation of a high-pass FIR filter block of FIG. 2.

The high-pass FIR filtering block 28 is shown in FIG. 4 and receives the data samples x(n) through x(N_FIR-1) from the time delay buffer of FIG. 3 and each sample is then multiplied by a filter coefficient before being summed with the product of an immediately previous sample times its coefficient. In determining the values of the coefficients use was made of a computer program called QE Design 1000 from Momentum Data Systems, Inc. of Fountain Valley, Calif. This software comprises a multi-platform advanced digital filter design package that is menu-driven and performs complex mathematical computations used in the design of digital filters. A designer using this software can compute the filter coefficients by inputting to the QED 1000 program input parameters including the filter type (high pass or low pass FIR filter), the sampling frequency (800 Hz), the pass band frequency (100 Hz), the stop band frequency (200 Hz), the number of filter taps, acceptable pass band and stop band ripple as well as other filter design parameters known to those skilled in the art.

The resulting sum of the products comprises an in-band noise signal on line 42 and it is scaled by a filter scale factor block 44. Once the coefficients to be used are determined, an in-band noise signal is determined using the resulting sum of the products and this in-band noise signal is multiplied by a scaling factor such that the data on line 45 comprises a scaled in-band noise signal. The appropriate scale factor (block 44) for use by the filter stages 14, 16, and 18 is computed using the formula:

$$\text{scale factor} = \sum_k |h\_fir_k|$$

where k is an index, 0 ... N-FIR-1 and $h\_fir_k$ comprises an array of coefficients. For the high filter stage 12 of FIG. 1, the scale factor is computed as:

$$\text{scale factor} = \frac{1}{1.5717} \sum_k |h\_fir_k|$$

Figure 5:
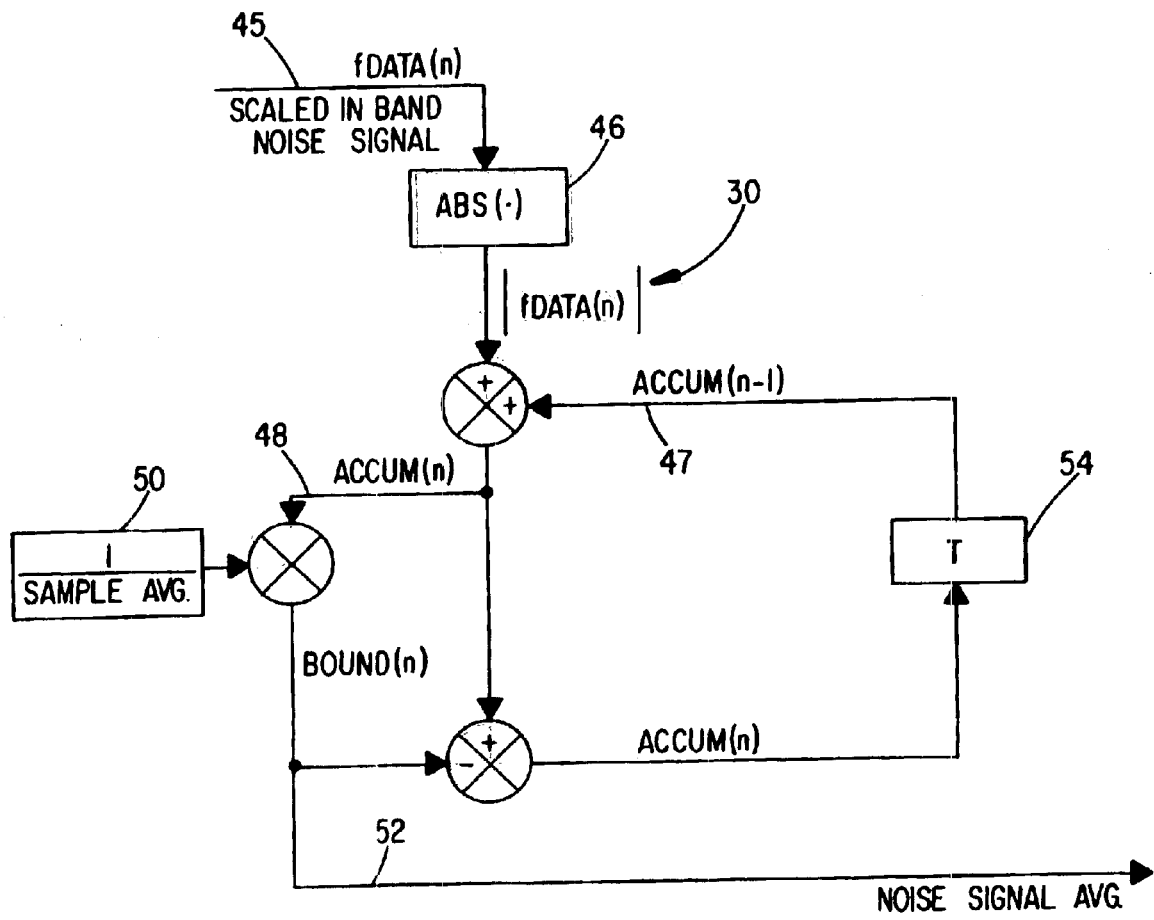
FIG. 5 is a more detailed block diagram representation of the dynamic noise level calculation block of FIG. 2.

Referring next to FIG. 5, the current filter data sample comes into the dynamic noise level calculation block 30 on line 45 and the absolute value thereof is calculated (block 46) before being summed with a preceding accumulator value, accum (n−1) on line 47 in forming the current accumulated value, accum (n) on line 48. The current accumulated value is divided by a sample average (block 50) in forming the "bound (n)" value on line 52. This same bound value is subtracted from the accumulated value and then delayed one sampling time (1.25 ms), represented by delay element 54, which then becomes the preceding accumulated value for the next filter data sample.

Figure 6:
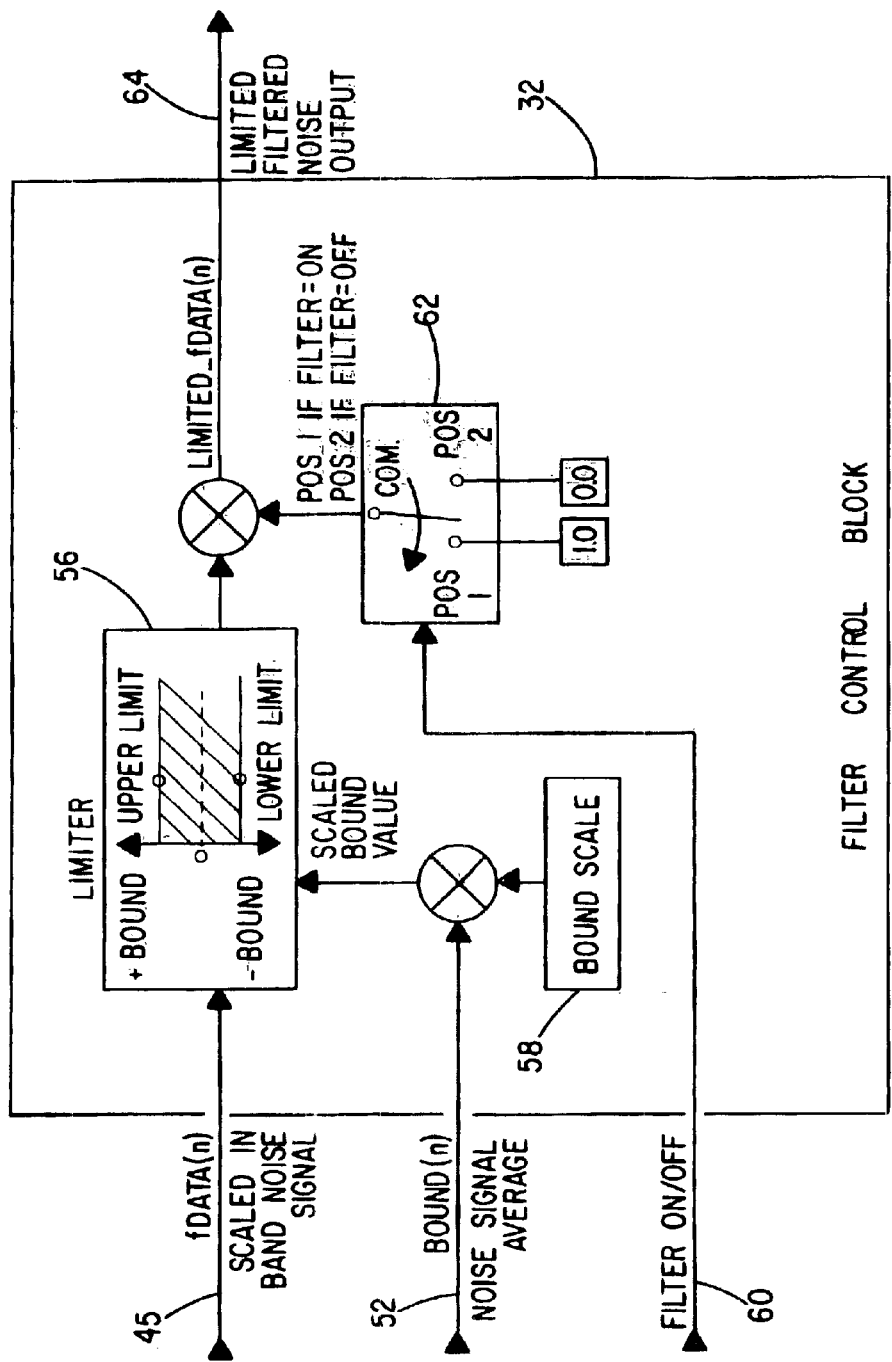
FIG. 6 is a block diagram representation of the filter control illustrated in FIG. 2.

Turning next to FIG. 6, there is illustrated in greater detail the filter control block 32 of FIG. 2. Here, the f data (n) on line 45 from the output of the high-pass fir filtering block 28 is limited so as to fall between an upper limit and a lower limit, as represented by block 56. A scale factor 58 applied to the bound (n) noise signal average on line 52 and is utilized by the limiter 56 in establishing the upper and lower bound limits. A filter on/off control signal on line 60 which is a binary 1 when the filter is on and a binary 0 when the filter is off, yields the limited filtered noise output on line 64 only when the filter control is in the "on" state (block 62).

Figure 7:
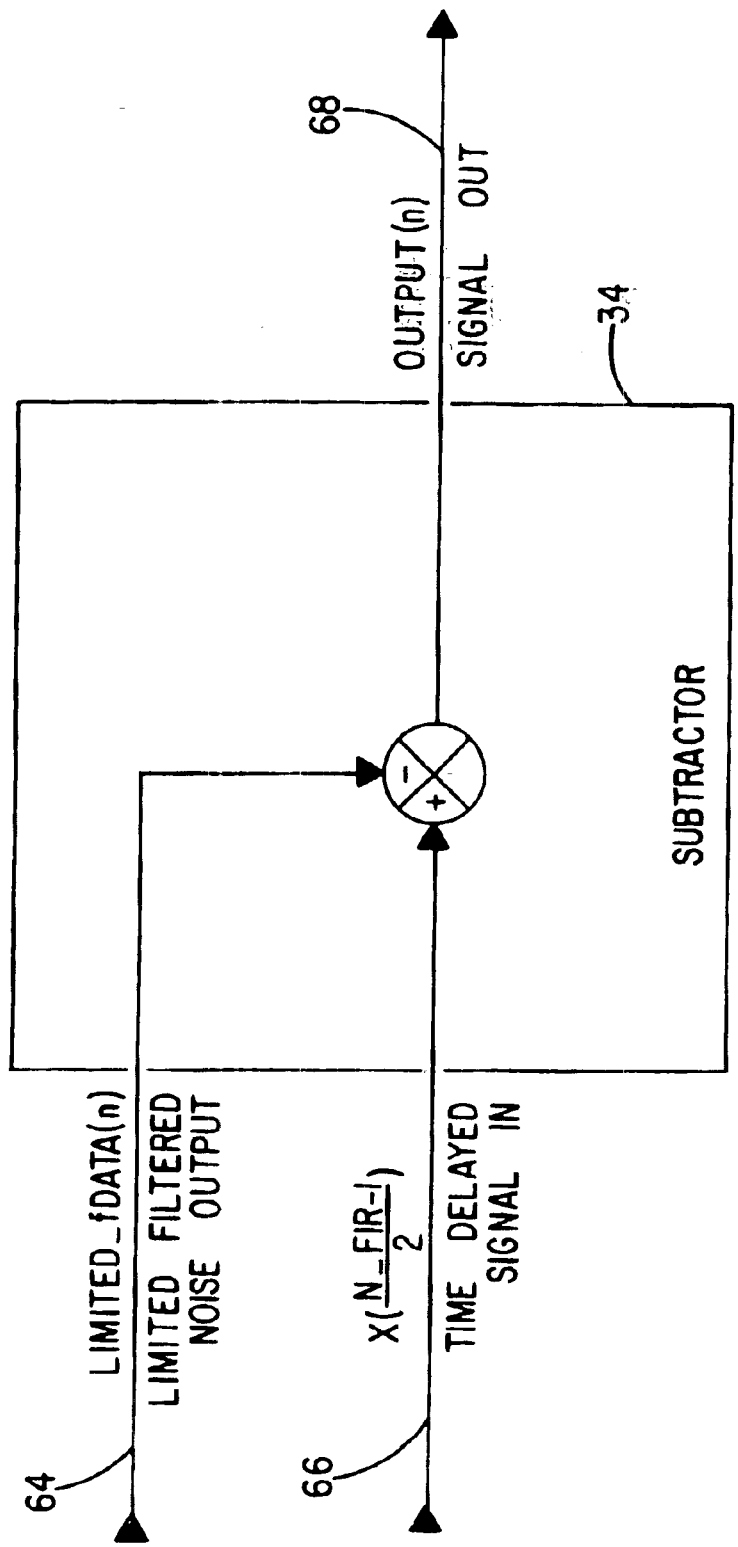
FIG. 7 is a more detailed block diagram representation of the subtracter used in the low-pass filter stage of FIG. 2.
Figure 8:
FIG. 8 is a key identifying the operational blocks used in FIGS. 2–7.
Figure 8:
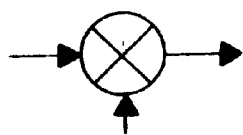
Figure 8:
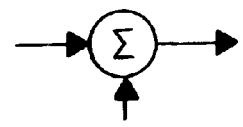
Figure 8:
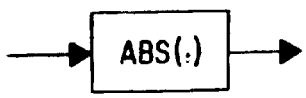
Figure 8:
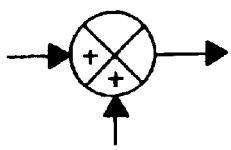

The subtractor 34 of FIG. 2 is shown in FIG. 7 and simply comprises the logic or software for subtracting the limited filtered noise output on line 64 from a timed delayed signal input from the buffer 26 on line 66. The particular buffer output used is the center of the $$\text{buffer} \times \left( \frac{N\_FIR - 1}{2} \right).$$

The center point of the buffer 26 is chosen in that here the coefficients are a maximum for the type of filters involved. The remaining coefficients are symmetrically disposed about the center value of the buffer. The output from the subtractor 34 on line 68 comprises the filtered signal output.

FIGS. 1 through 8 schematically depict the make-up of each of the filter stages 12, 14, 16 and 18 shown in FIG. 1 of the drawings using symbology familiar to those working with control systems. To aid in a better understanding of the invention, there is also provided in FIGS. 9–31 software flow charts depicting the algorithms which may be executed by a conventional microprocessor in implementing the filter stages illustrated in FIG. 1 of the drawings.

Figure 9:
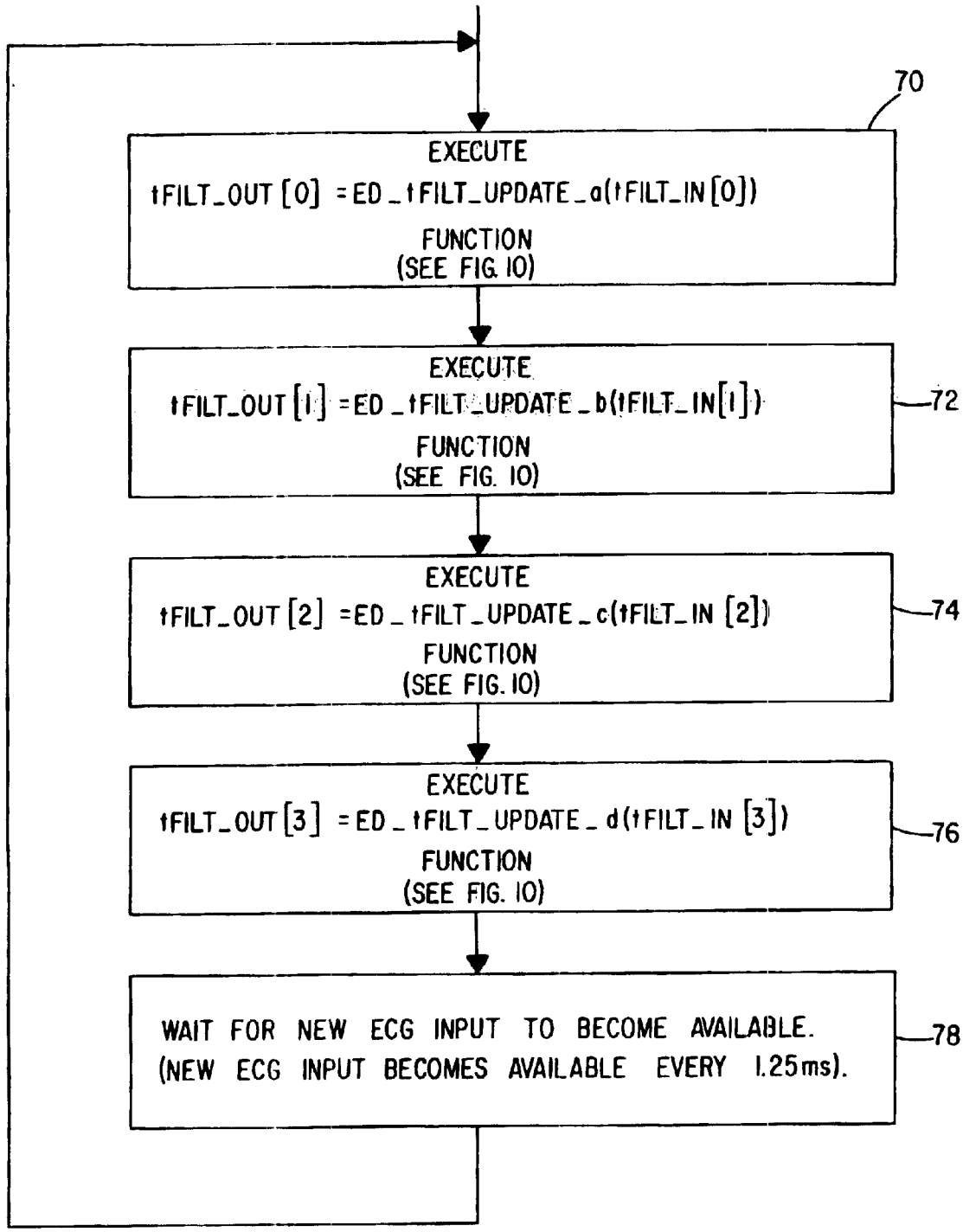
FIG. 9 is a top level flow diagram for the software implementing the ECG low-pass filter as applied ECG vectors I, II, III and V.

Referring to FIG. 9, there is shown the top level of program execution. Assuming an analog-to-digital converter operating at 800 Hz, every 1.25 ms the software functions represented by FIG. 9 are called in order to perform the low distortion ECG signal filtering. As those skilled in the art appreciate, the standard ECG surface electrodes appropriately positioned on the body. Potential differences are represented by vector quantities, which include vector I, vector II, vector III, and vector V. In C language programming, vector quantities are represented by bracketing. Thus, for example, block 70 in FIG. 9 represents the operation of updating filter outputs by updating vectors I, II, III and V which are for simplification respectively referred to by the letters a, b, c, and d. See block 70–76. Once each of the vectors is updated, the software waits for a new ECG input to become available which occurs every 1.25 ms. See block 78 in FIG. 9.

Figure 10:
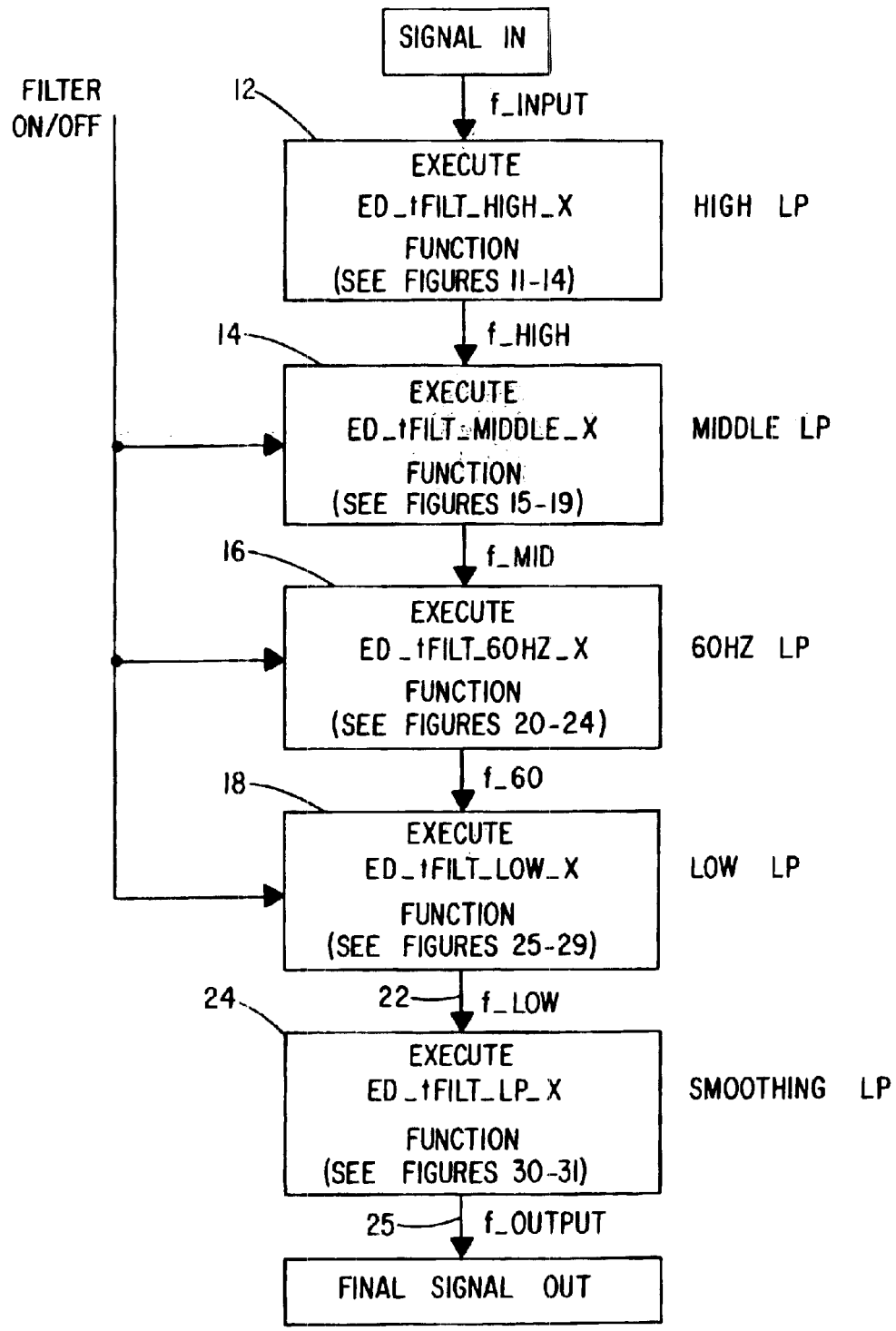
FIG. 10 is a software flow diagram which when called performs the filtering functions represented by FIG. 1 of the drawings.

The manner in which the updating is achieved for each of the vectors involved is illustrated by the flow diagram of FIG. 10. Comparing FIG. 10 to FIG. 1 of the drawings, a filter input signal is subjected to digital signal processing in a programmed microcomputer to implement the high low-pass (100 Hz) filter function (block 12 of FIG. 1) and the output of the high LP processing (f_high) is applied as an input to the middle LP (80 Hz) stage 14 which, in turn, supplies the f_mid signal as an input to the 60 Hz low-pass filter stage 16. Its output, f_60, then goes to the low low-pass filter stage 18. Finally, the filtered output f_low on line 22 is subjected to smoothing in low-pass filter stage 24 resulting in the signal f_output 55 which is the final "signal out". In FIG. 10, the value x can take on the values a, b, c and d representative of the ECG vectors I, II, III and V meaning that the same execution steps are carried out on each vector.

The high low-pass filter execution involves the steps set out in the flow diagrams comprising FIGS. 11–14 of the drawings. Likewise, the remaining low-pass filter stages 14, 16, 18 and 24 execute in accordance with the flow diagrams indicated therewith. Thus, FIGS. 9 and 10 represent a hierarchical organization such that an explanation of the algorithm for one of the filter stages should suffice as a complete explanation of the software implementation of the remaining filter stages.

Figure 11:
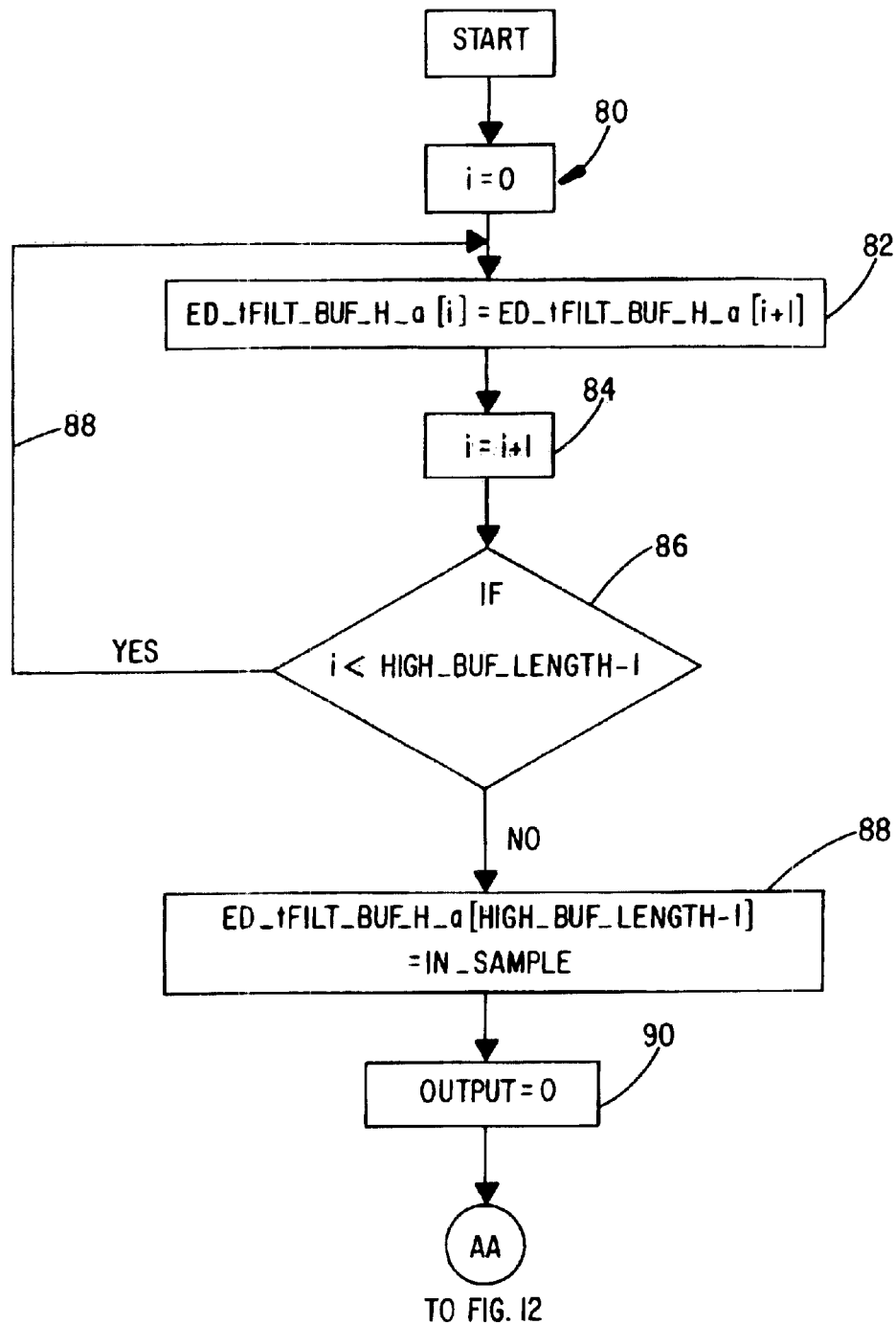
FIGS. 11–14 illustrate the software operations implementing the high low-pass filter stage 12 of FIG. 1.
Figure 12:
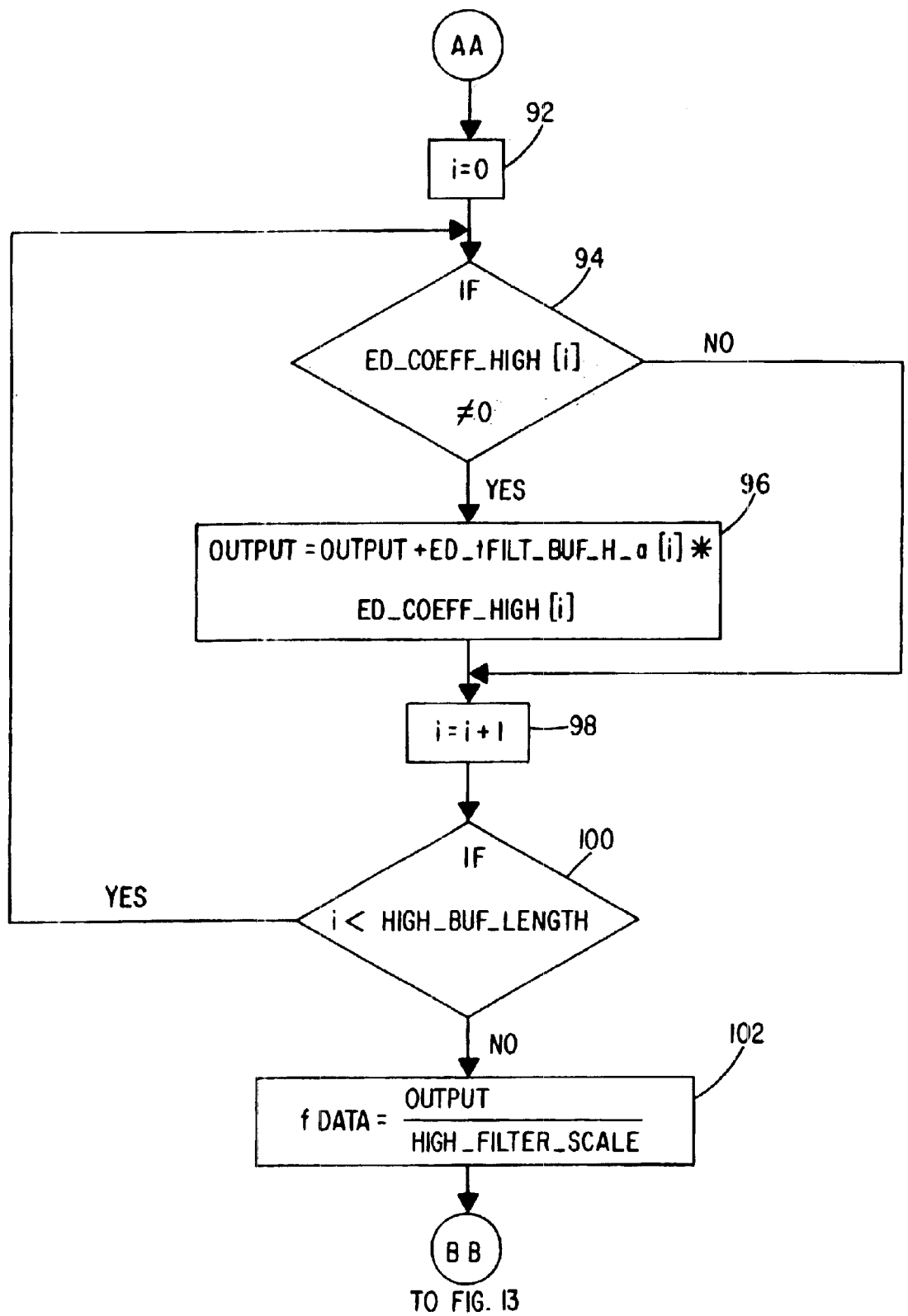

In FIG. 11 at block 80 an index, i, is set equal to 0 and a buffer is loaded in accordance with blocks 82, 84 and 86. In block 82, what was sample 0 becomes sample 1, which is then followed by step 84 where the index is incremented by 1. A test is made at block 86 to determine whether the index, i, has become equal to one less than the length of the high buffer, i.e., equal to 24. If not, control loops back, via path 88, to the input of block 82 where the input data is again shifted down the buffer. This operation continues until the test at block 86 reveals that the index has reached 24 at which point the buffer is fully loaded making element 24 in the buffer available for storing the input sample. See block 88. Next, an output variable is set to 0 (block 90) and control passes to the connection point AA at the top of FIG. 12. Here again, as indicated by block 92, an index, i, is set to 0 and a test is made at decision block 94 to determine if the coefficient of the high filter is unequal to zero. If it is not, the next operation represented by block 96 is skipped as a way of conserving time. If the coefficient is unequal to zero, then the output is made equal to the preceding output which is summed with the product of the buffer value and its coefficient. The index i is then incremented at block 98 and these operations continue until the test at block 100 indicates that the index has reached the buffer length of the high buffer, i.e., 25. Thus, the loop comprising blocks 94, 96, 98 and 100 develops a sum of the products of the buffer elements and the corresponding coefficients. When the test at block 100 reveals that the index has become equal to the buffer length, the operation represented by block 102 is performed and the filter data is formed by scaling the output.

Figure 13:
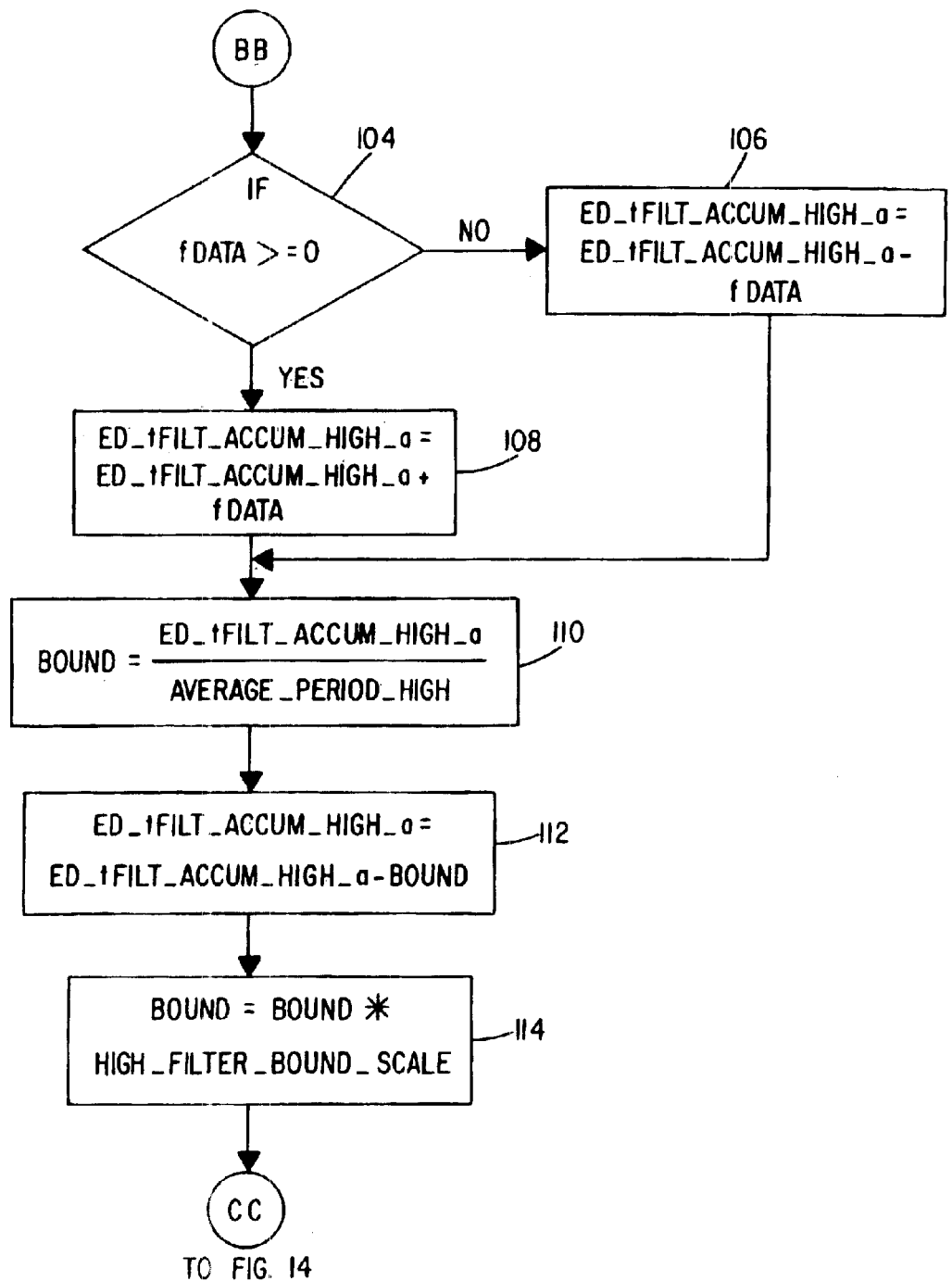

Turning next to FIG. 13, the next operation in the sequence is to test whether the filter data is greater than or equal to zero. See decision block 104. If not, the high filter accumulator is made equal to the high filter accumulator less the filter data (block 106). If, however, the test at decision block 104 shows that the filter data is greater than or equal to zero, the high low-pass filter accumulator is set equal to its previous value plus the filter data at block 108. The net result of the operations represented by block 106 and 108 is to form the absolute value of the filter data which corresponds to what was done in the representation depicted in FIG. 5 of the drawings. The accumulated value in block 110 is then averaged to yield the bound value. Next, as represented by block 112, the bound value is subtracted from the accumulated value and the accumulated value is then overwritten. Next, the bound value is multiplied by a scale factor such as two or three (block 114).

Figure 14:
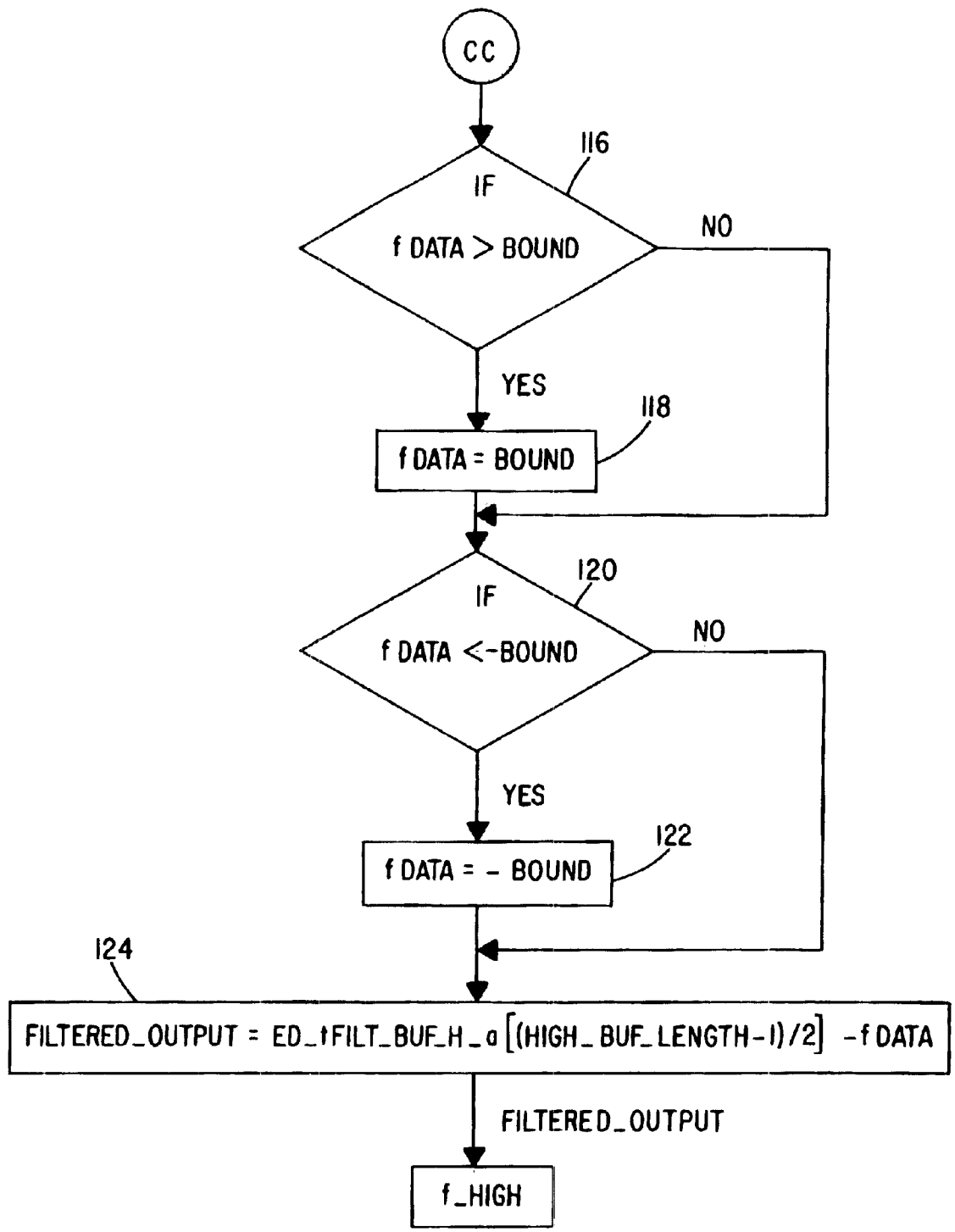
Figure 15:
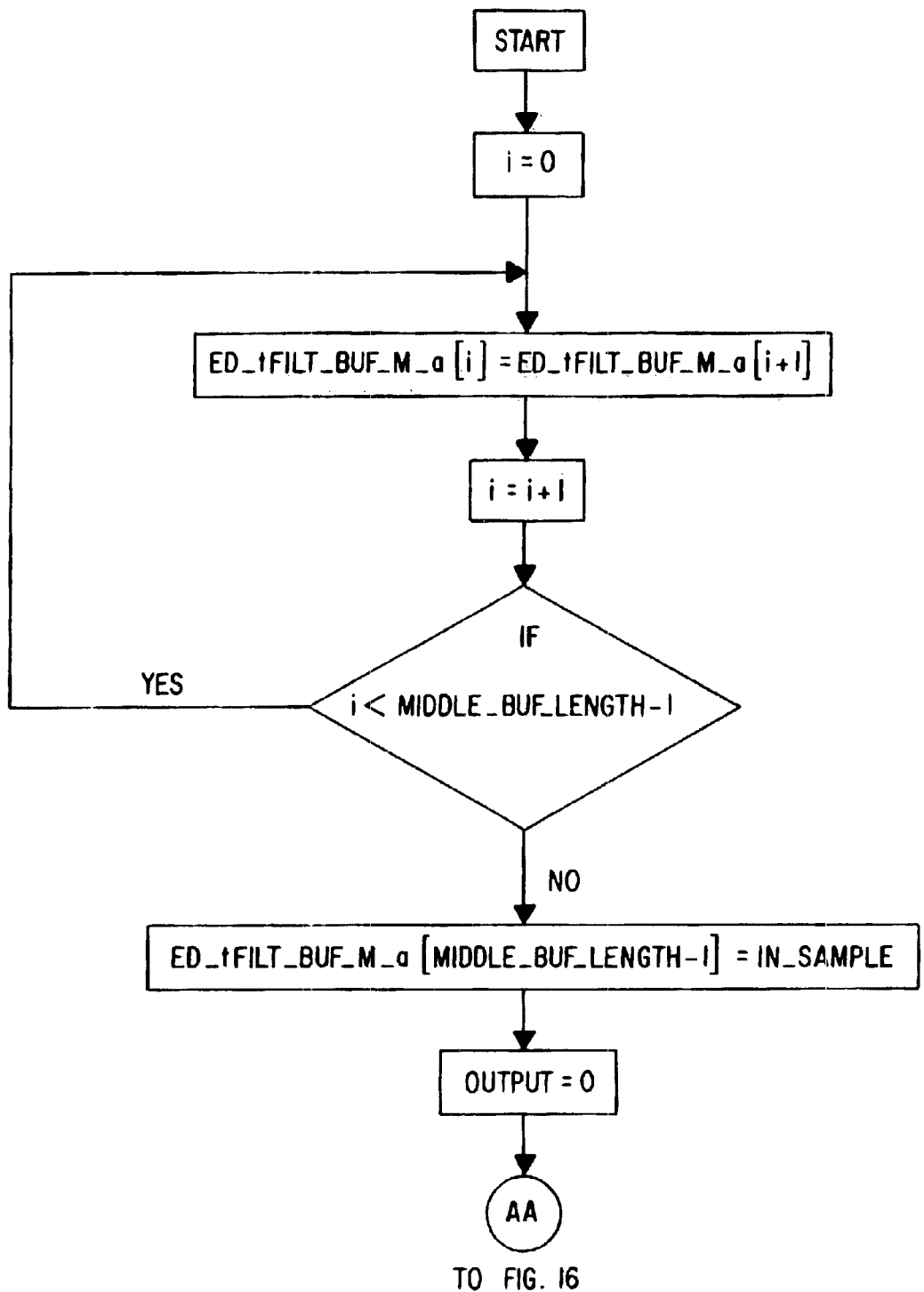
FIGS. 15–19 illustrate the software implementation of the middle low-pass filter 14 of FIG. 1.
Figure 16:
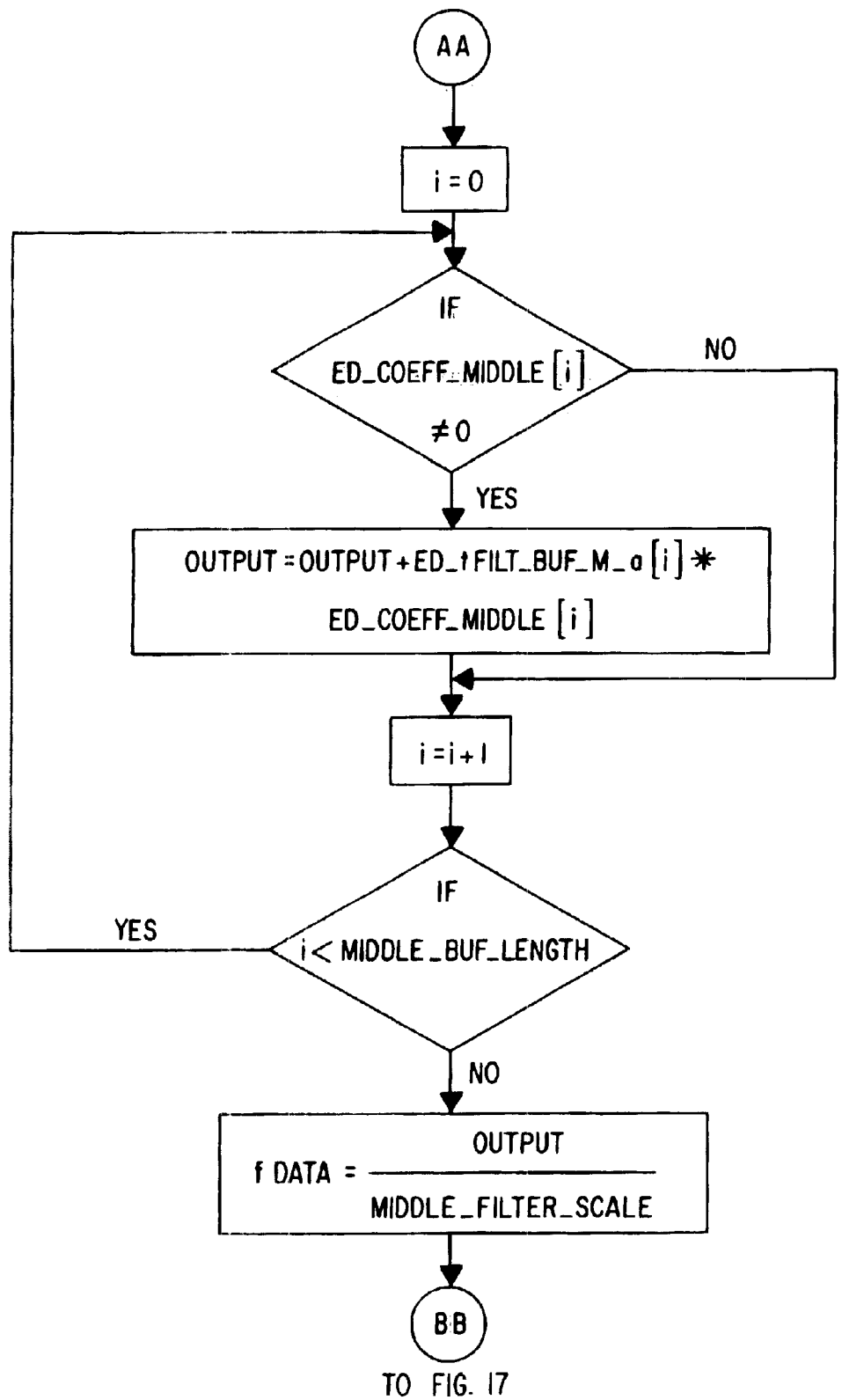
Figure 17:
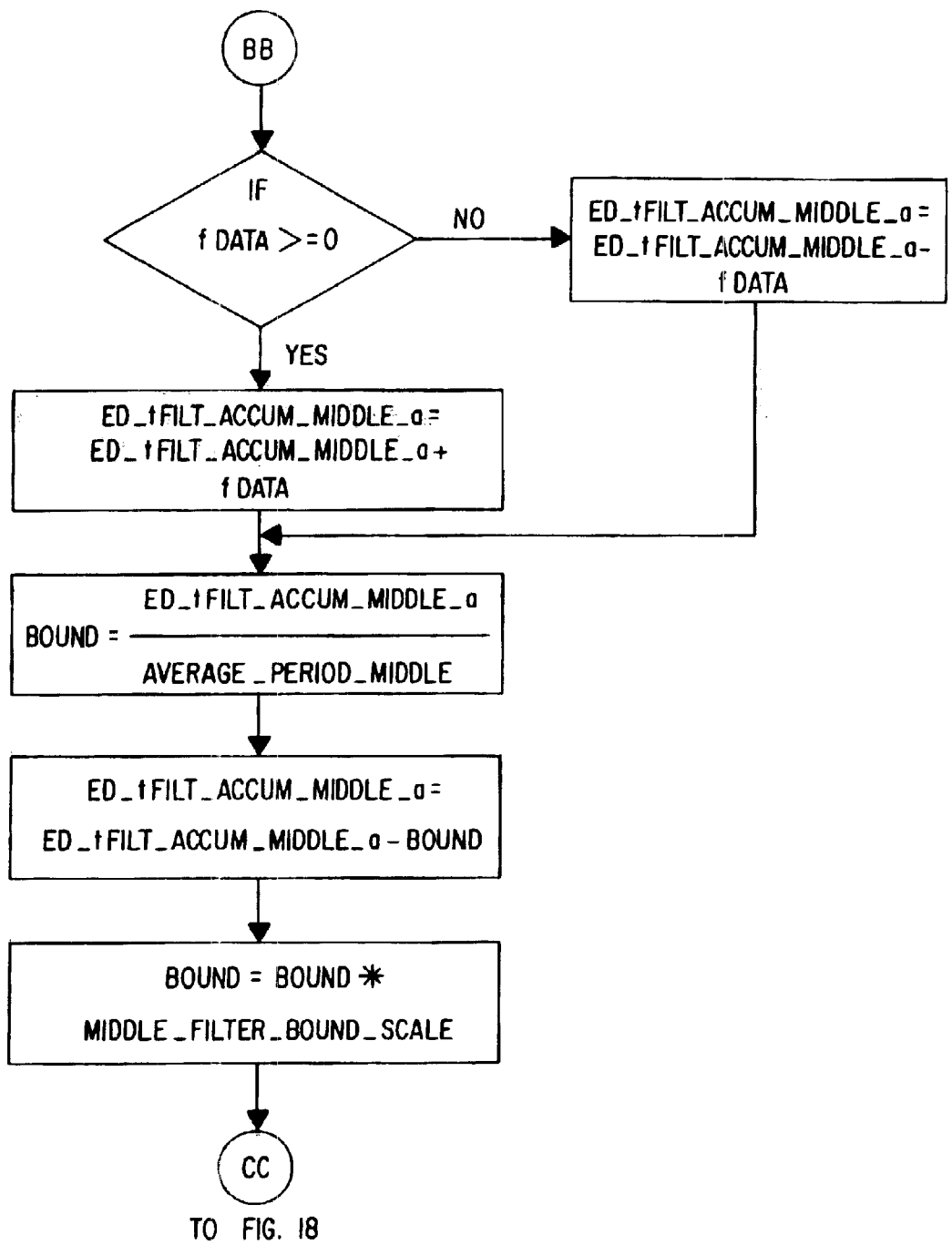
Figure 18:
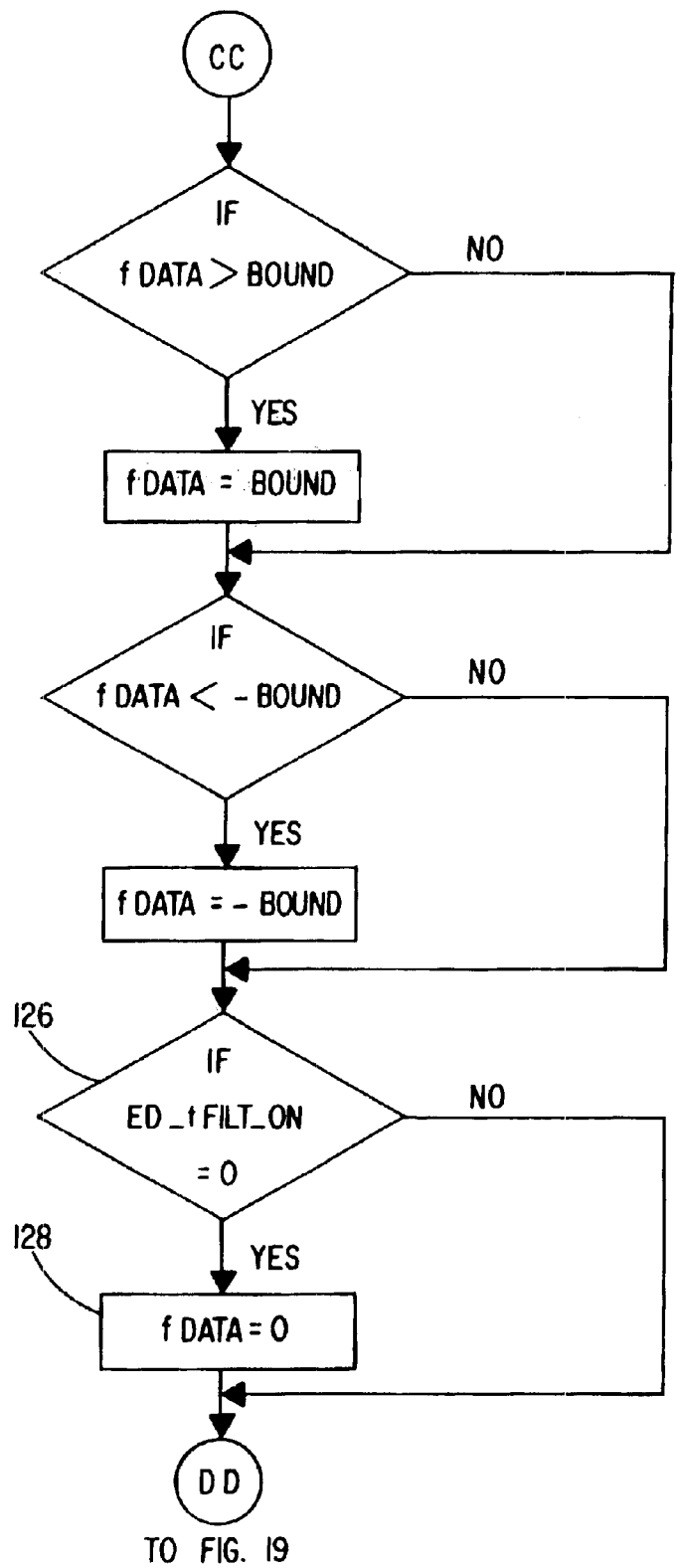
Figure 19:
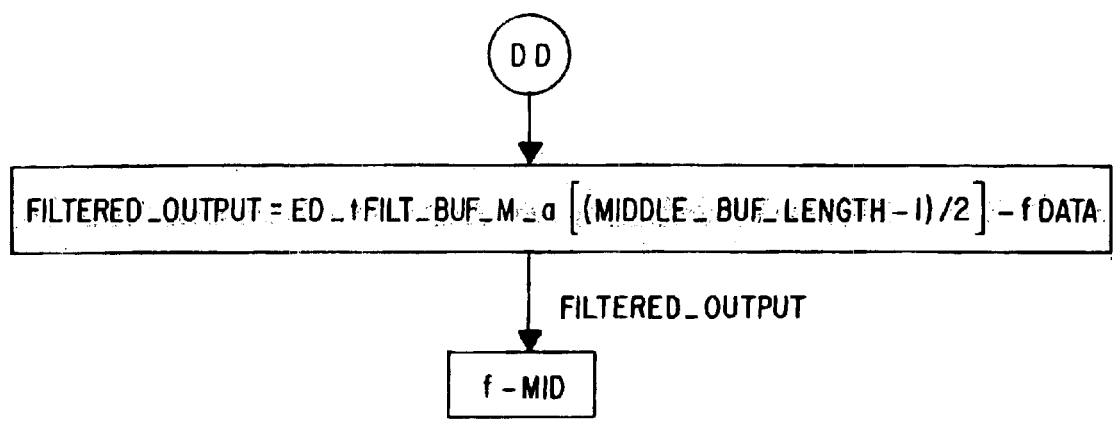
Figure 20:
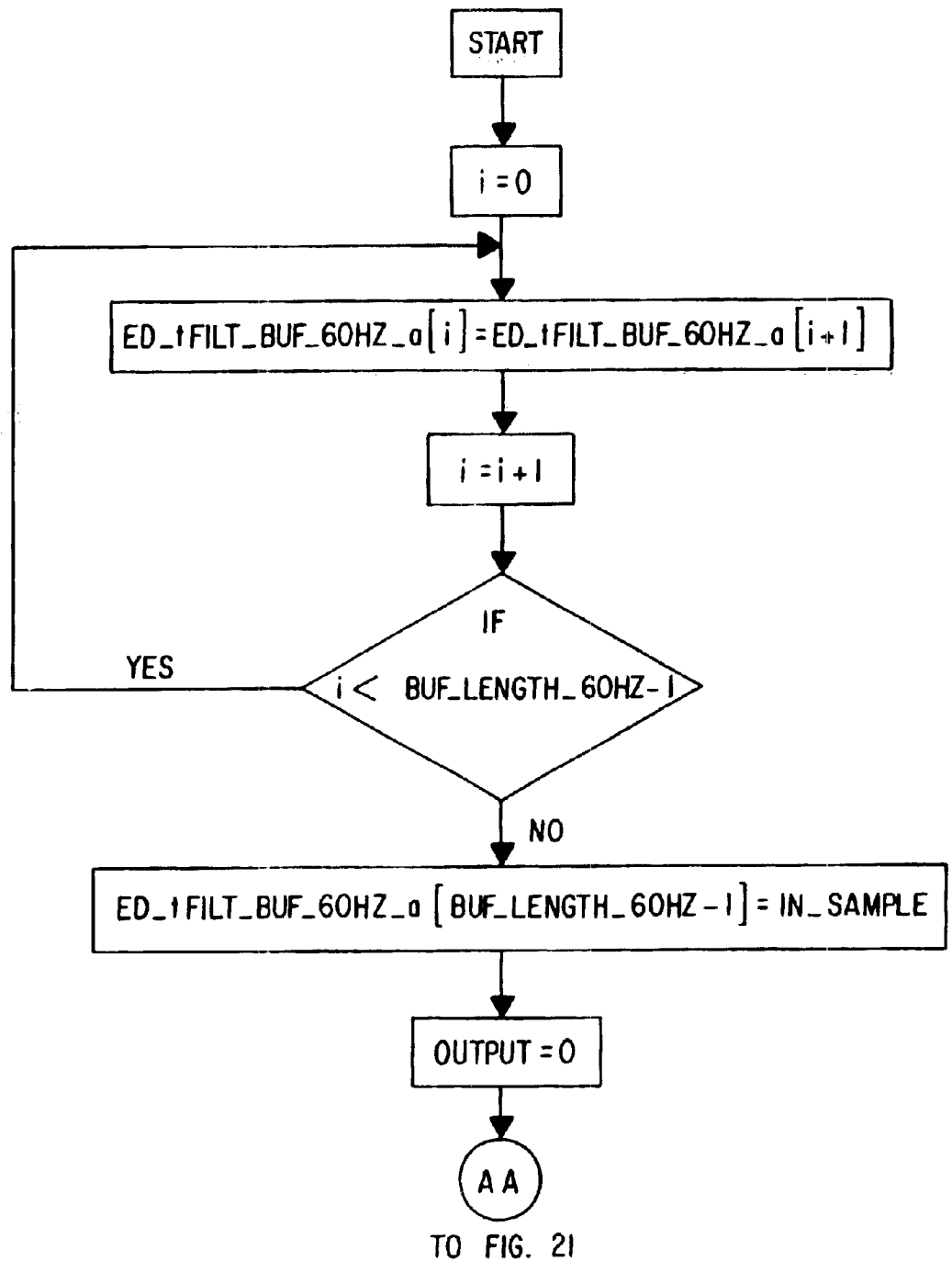
FIGS. 20–24 illustrate the software implementation of the 60 Hz low-pass filter 16 of FIG. 1.
Figure 21:
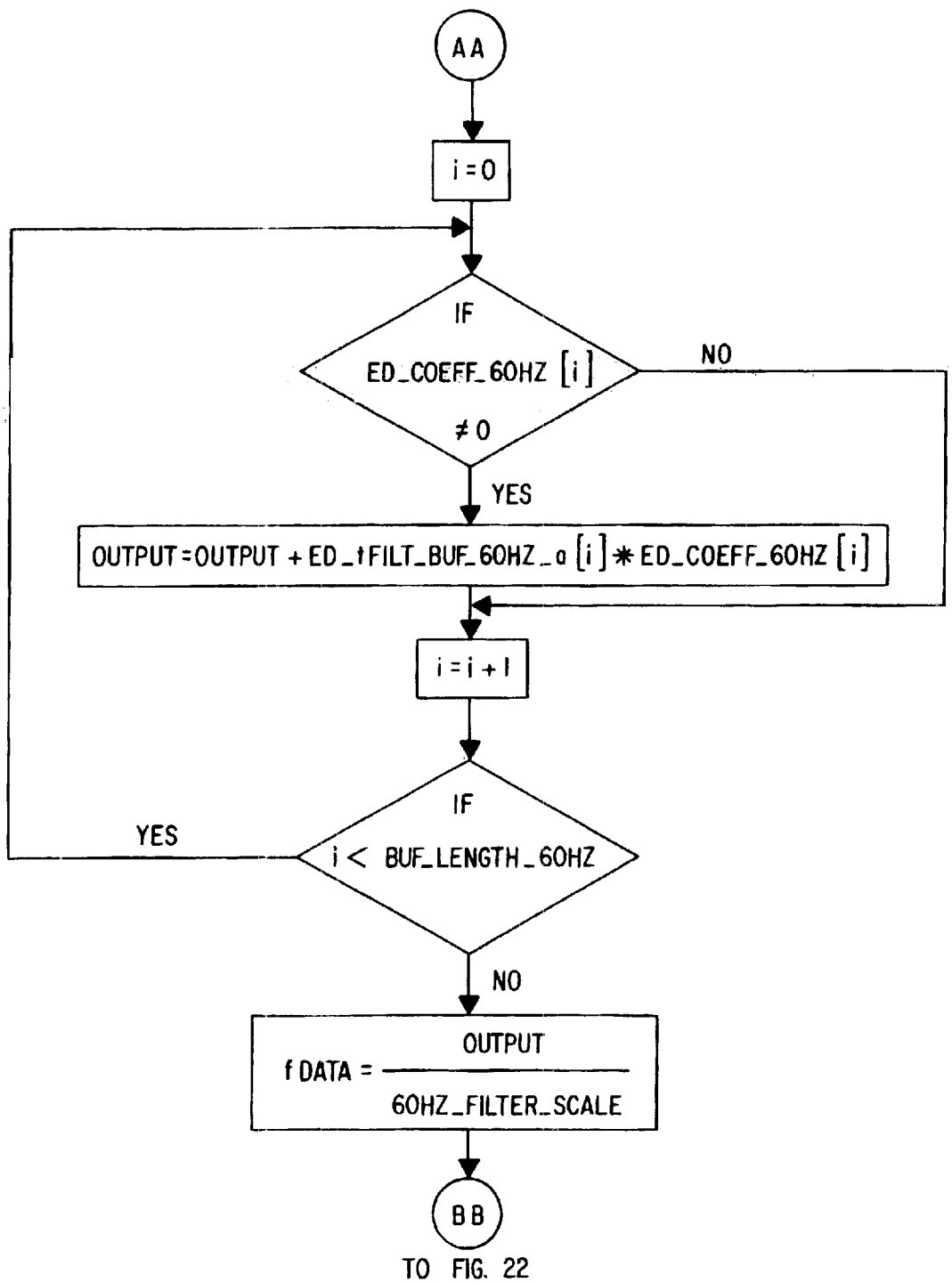
Figure 22:
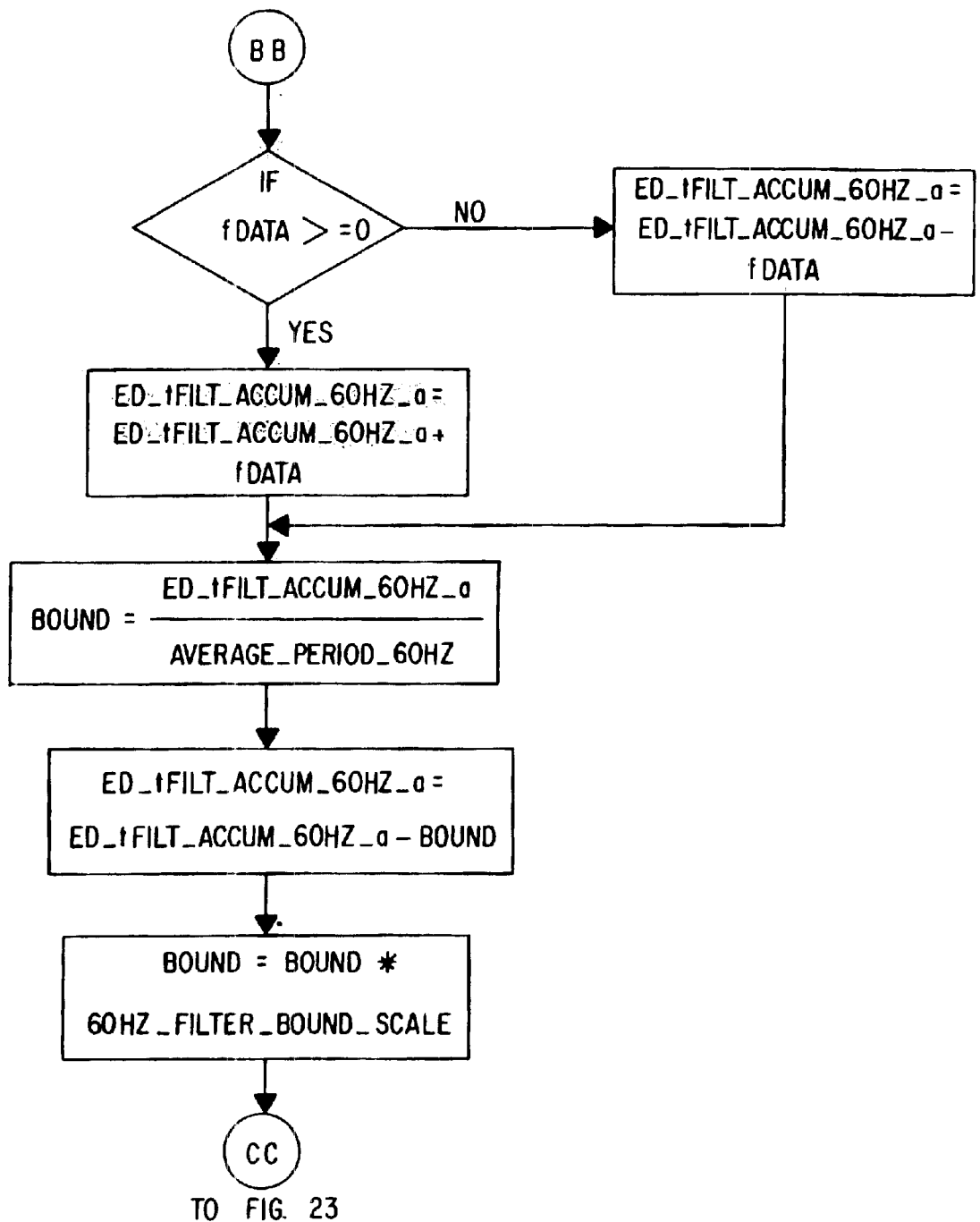
Figure 23:
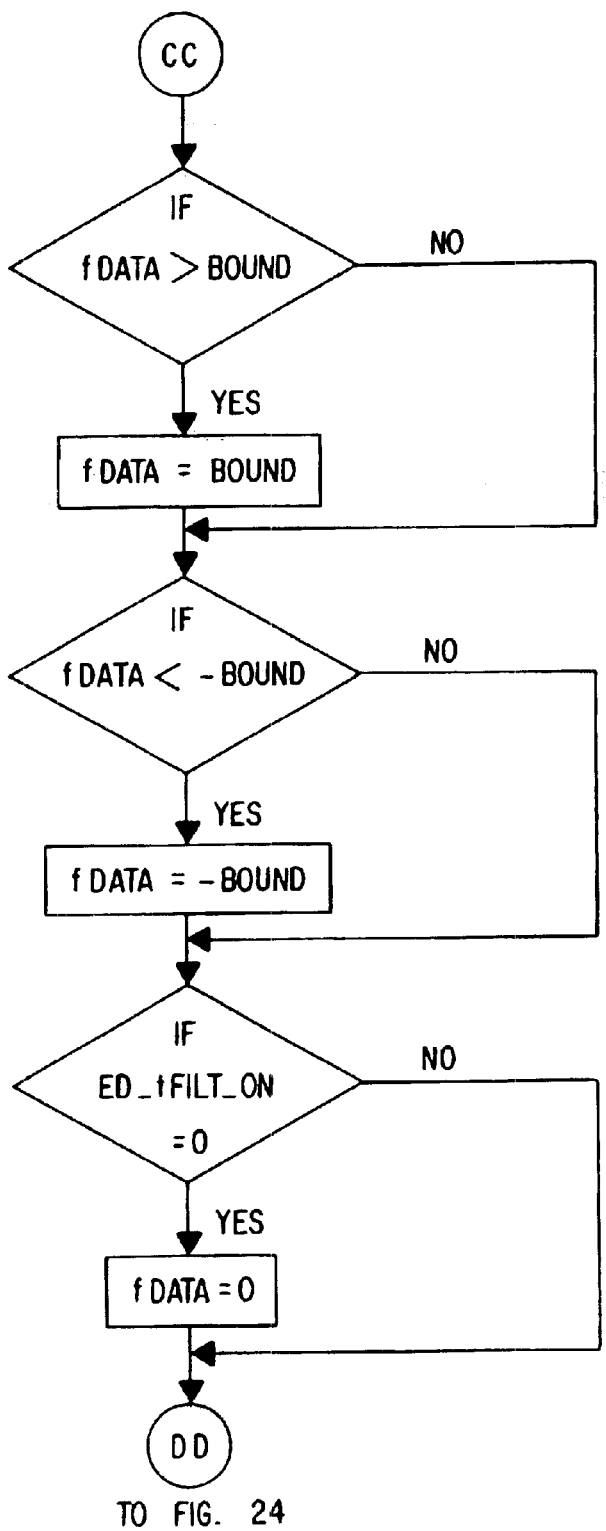
Figure 24:
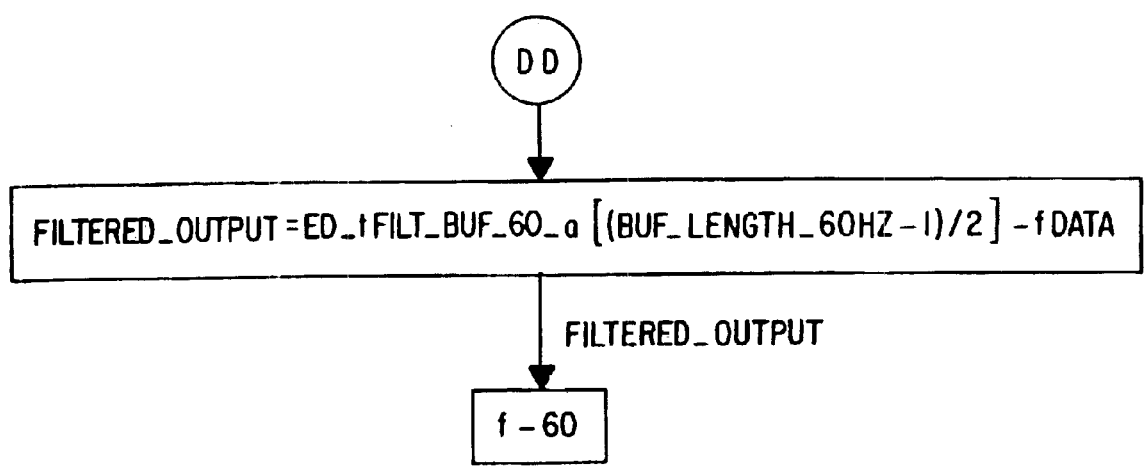
Figure 25:
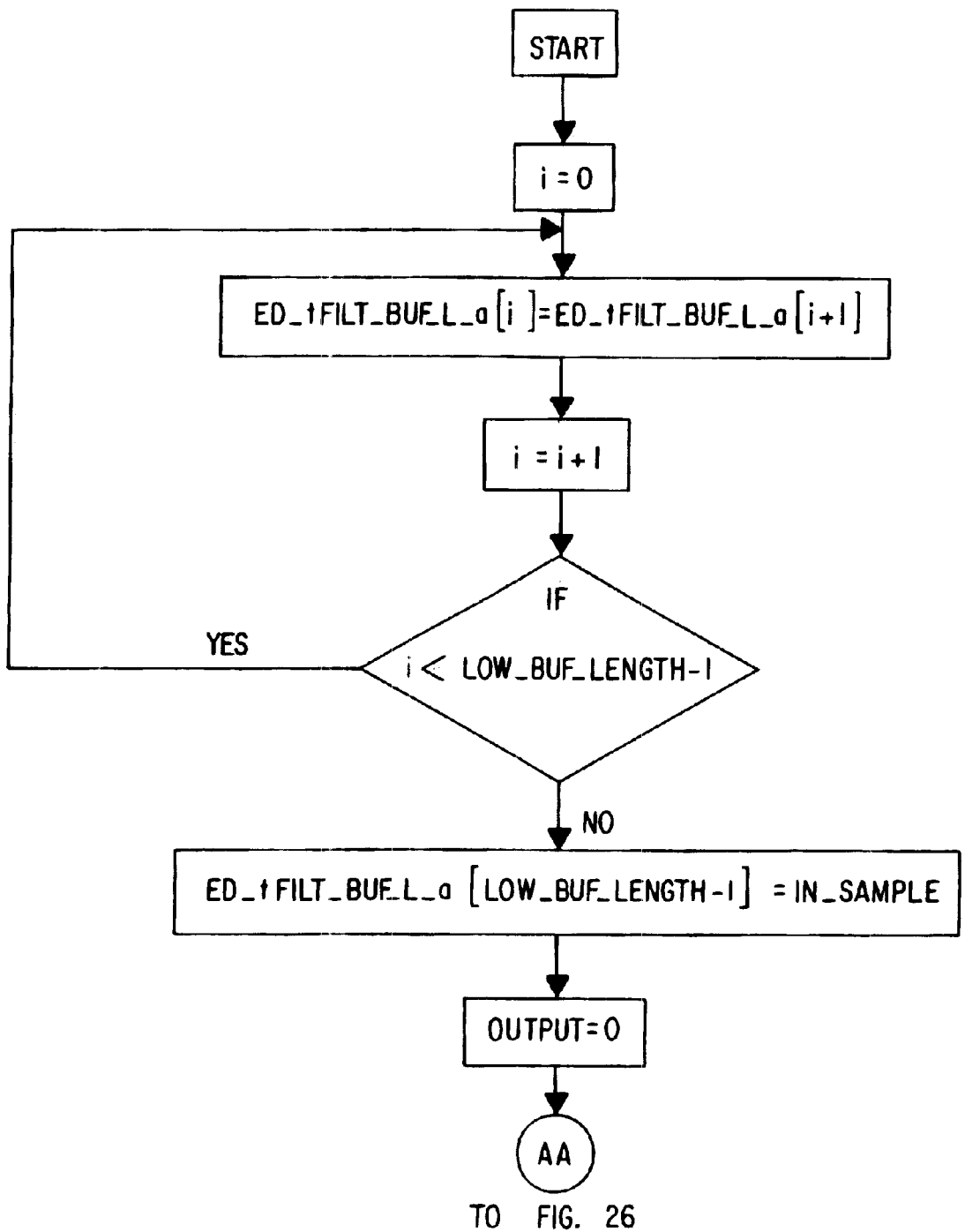
FIGS. 25–29 illustrate the software implementation of the low low-pass filter 18 of FIG. 1.
Figure 26:
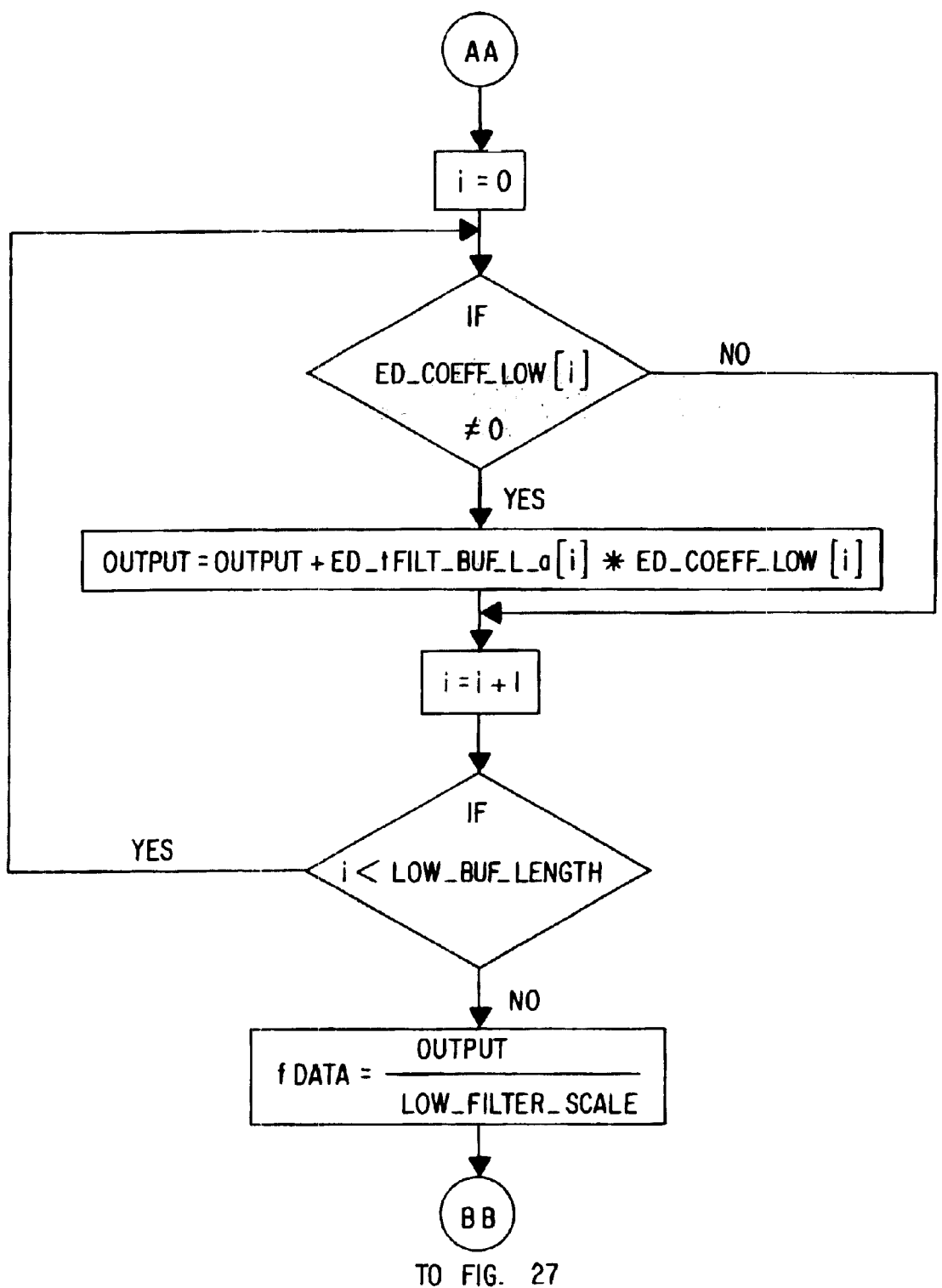
Figure 27:
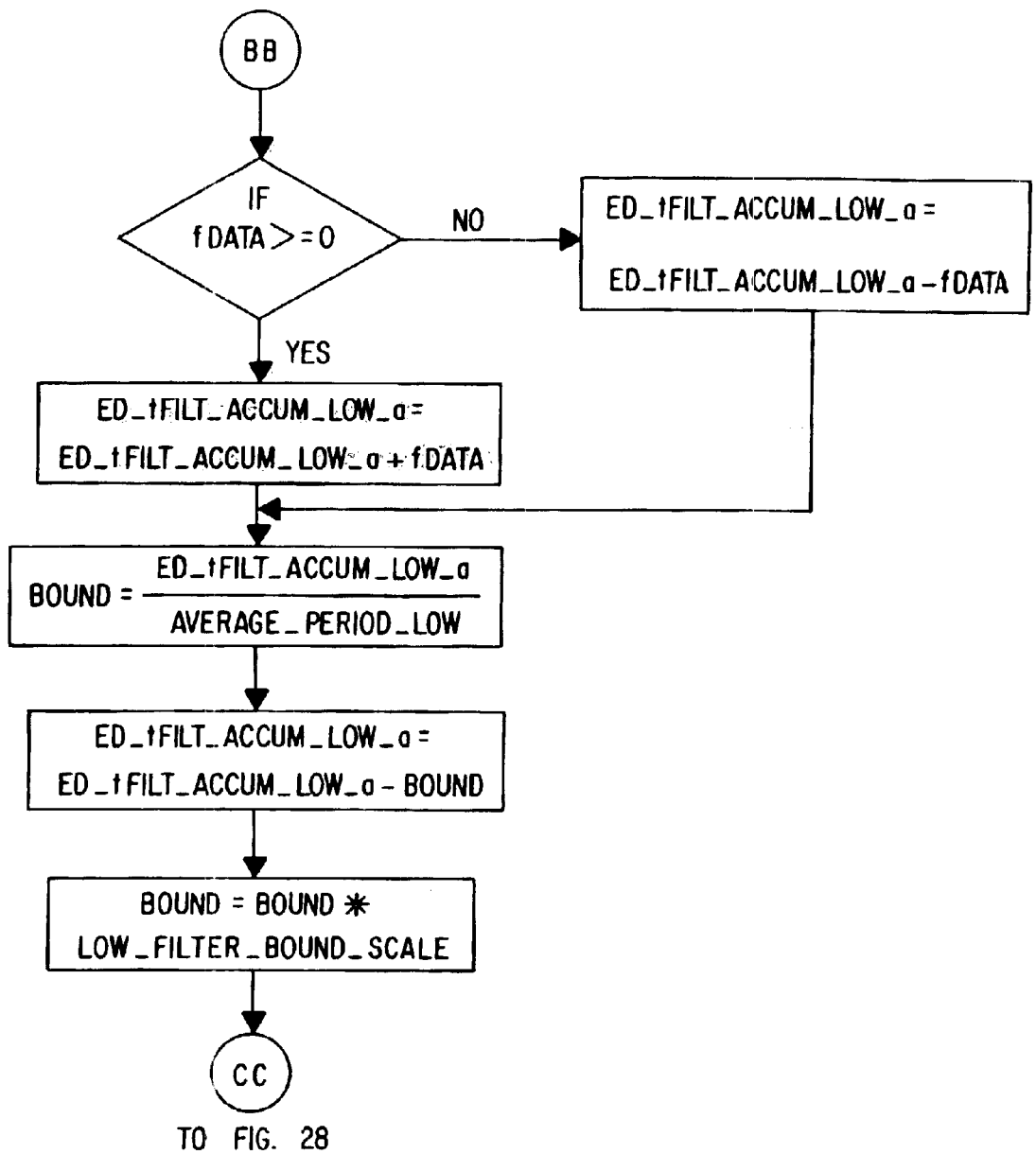
Figure 28:
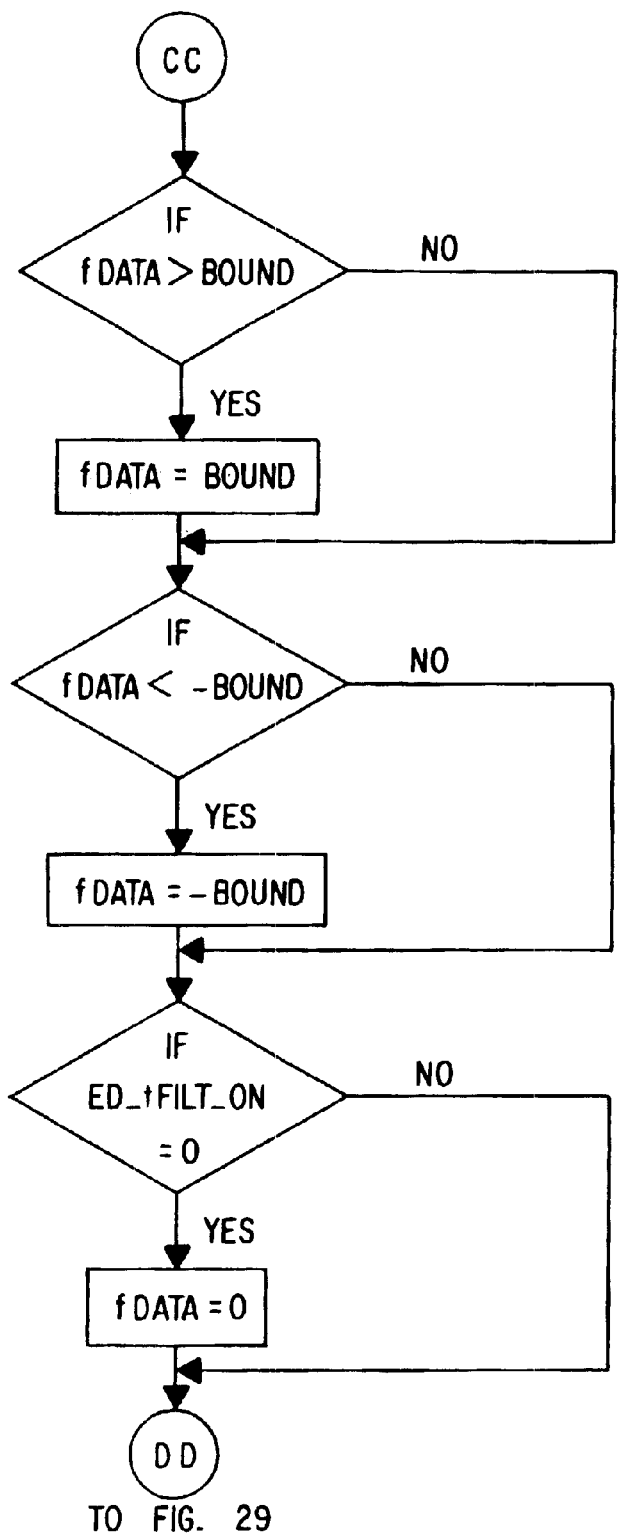
Figure 29:
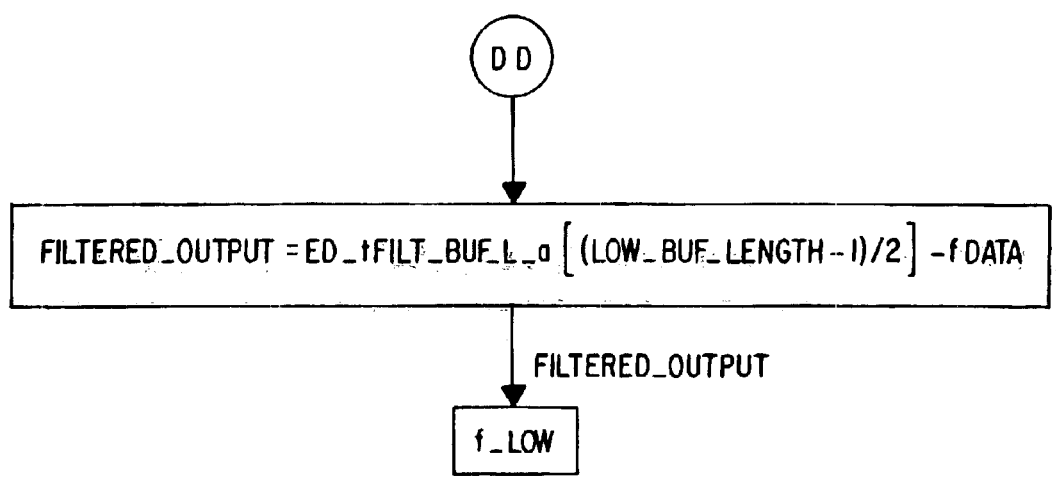
Figure 30:
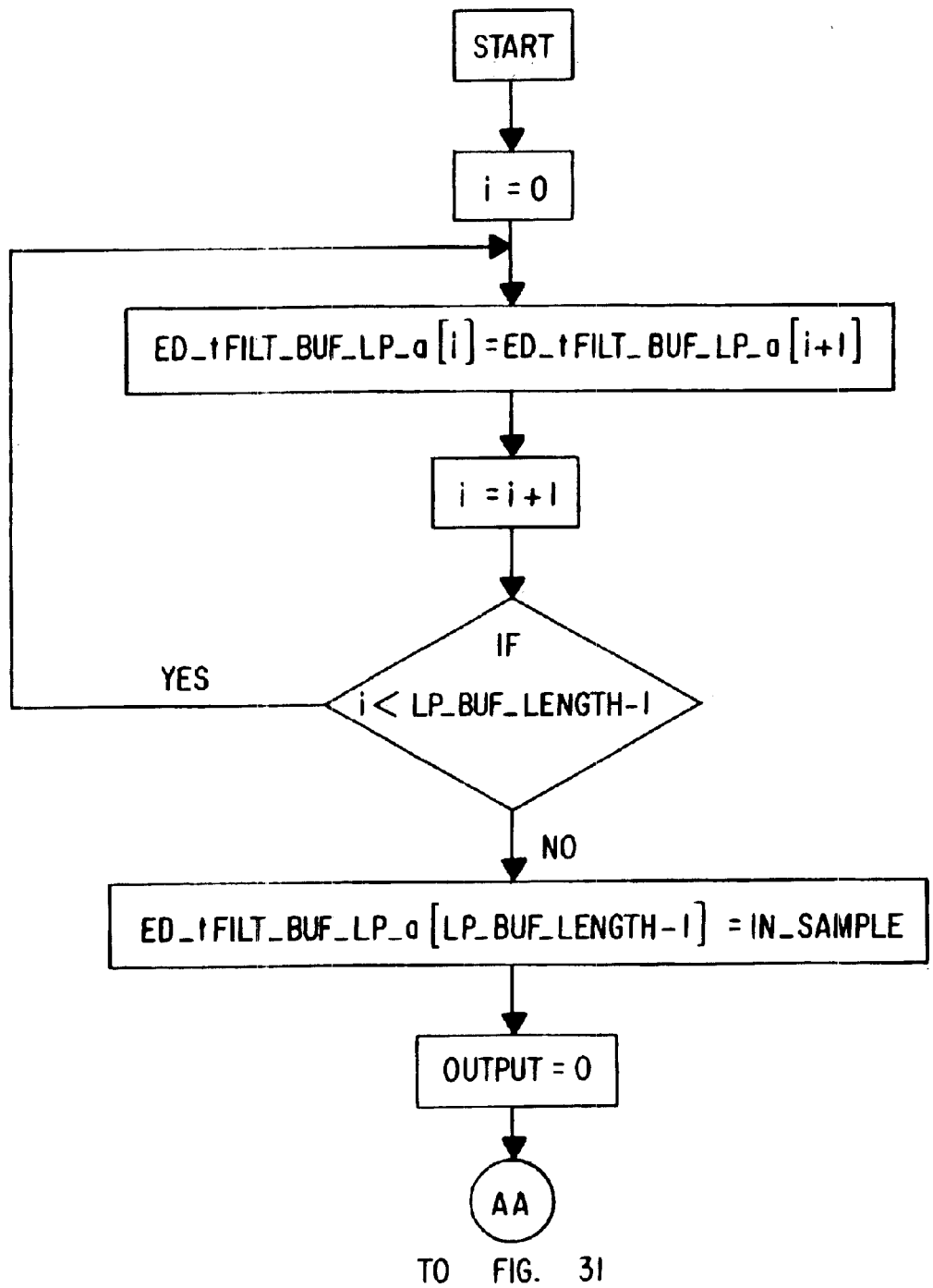
FIGS. 30 and 31 illustrate the software implementation of the smoothing low-pass filter 24 of FIG. 1.
Figure 31:
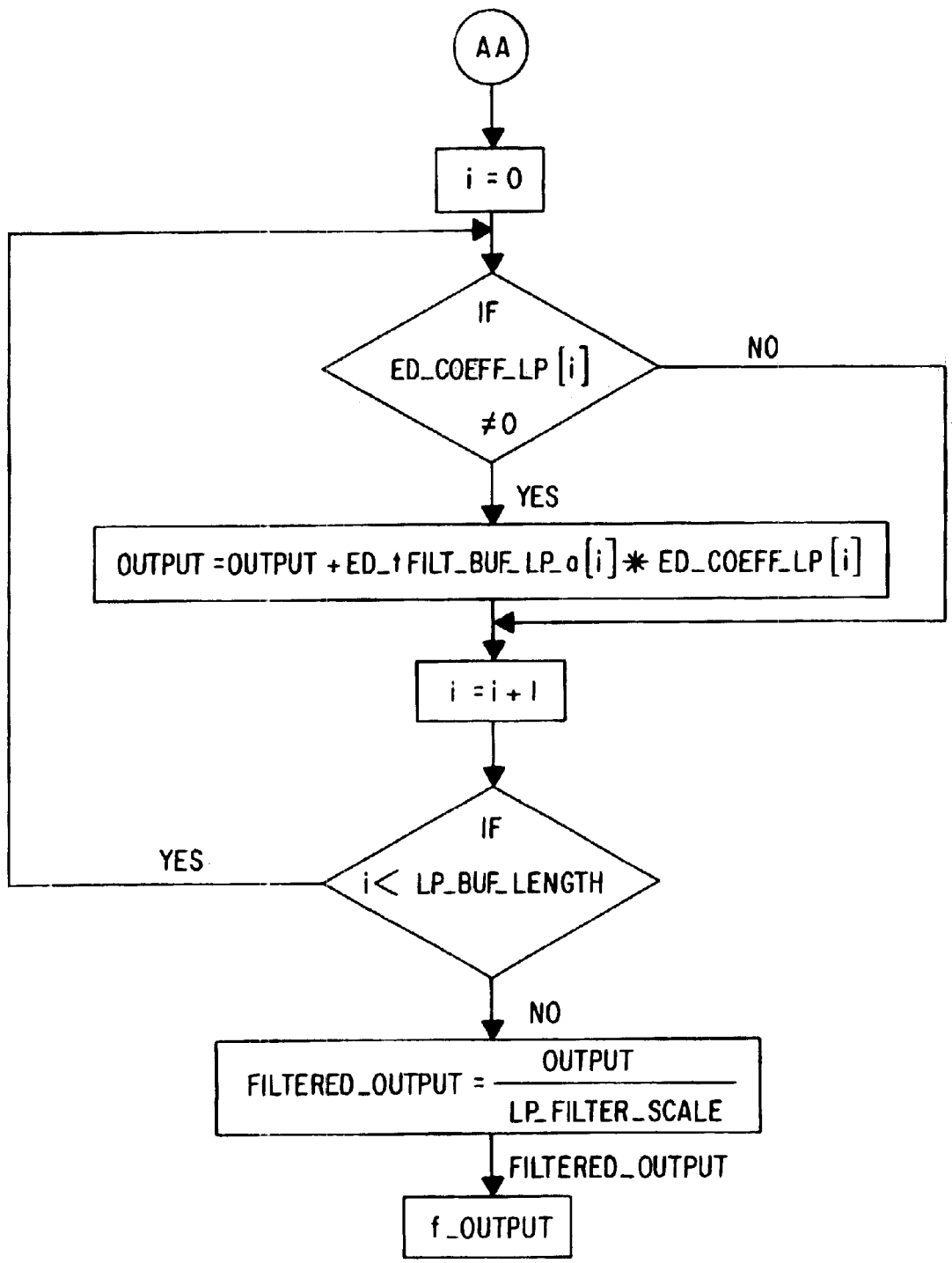

Turning next to FIG. 14, there is shown the flow diagram of the operations used to bound the filter data values. At block 116, a test is made to determine whether the filtered data exceeds its bound and, if so, it is set equal to the bound (block 118). If the filtered data is not greater than the bound and processing continues at block 120. A test is made at block 120 to determine whether it is less than the negative bound and, if so, the filtered data is set to the negative bound (block 122) and processing continues at block 124. If not, the processing continues at block 124. The filtered output (block 124) becomes equal to the quantity stored in the exact middle of the buffer minus the filter data. As mentioned above, the middle of the buffer is the location at which the length of the $$\frac{high\_buffer\_length - 1}{2}$$

pertains. This completes the software execution for the high low-pass filter stage 12.

FIGS. 15–19 are substantially identical to the flow diagrams of FIGS. 11–14 except that they now pertain to the middle low-pass buffer stage 14. Having described in detail the flow charts for the high low-pass filter, it is believed unnecessary to repeat the explanation for the middle low-pass filter and for the 60 Hz and the low low-pass filter stages 14, 16 and 18 which, respectively, comprise FIGS. 15–19, 20–24 and 25–29. One point bears mention, however, and that relates to FIG. 18, which is substantially the same as the flow diagram of FIG. 14, except for the inclusion of block 126 which tests whether the on/off control is on or off. Specifically, when the test at decision block 126 determines that the control signal is a zero, it means that the middle filter is off and the filter data is set to zero (block 128). If the filter is on, control moves to the connector DD at the top of FIG. 19 where the operation identical to that of block 124 of FIG. 14 is carried out.

FIGS. 20–24 and 25–29 depicting the 60 Hz and low low-pass filter stages 16 and 18 of FIG. 1 merely repeat the same sequence of operations as already explained, nothing further need be said concerning those drawings and they are included primarily for the sake of completeness.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of processing ECG signals comprising the steps of:

(a) applying amplified analog waveforms representative of ecg vectors to an analog-to-digital converter;

(b) obtaining digital values from the analog-to-digital converter representative of the amplitude of the ecg vector signals at discrete sampling times;

(c) storing the digital values in a multi-stage time delay buffer;

(d) computing from the stored digital values a scaled noise signal falling within a first predetermined frequency band;

(e) dynamically determining upper and lower limits for the scaled noise signal computed in step (d); and (f) subtracting the signal computed in step (d) from a data sample stored in a predetermined stage of the time delay buffer to yield an output signal devoid of noise falling within said first predetermined frequency band.

2. The method of claim 1 and further including the steps of applying said output signal to a further time delay buffer and repeating steps (d), (e) and (f) on the stored digital values in the further time delay buffer, step (d) involves a second predetermined frequency band different from said first predetermined frequency band.

* * * * *